(12) United States Patent
Langley et al.

(10) Patent No.: US 10,156,599 B2
(45) Date of Patent: Dec. 18, 2018

(54) APPARATUS AND METHOD FOR DETERMINING STATISTICS OF ELECTRIC CURRENT IN AN ELECTRICAL SYSTEM EXPOSED TO DIFFUSE ELECTROMAGNETIC FIELDS

(71) Applicants: Dassault Systemes Simulia Corp., Johnston, RI (US); Paul G. Bremner, Del Mar, CA (US)

(72) Inventors: Robin Stewart Langley, Cambridge (GB); Andrea Barbarulo, Paris (FR); Louis Kovalevsky, Cambridge (GB)

(73) Assignees: Dassault Systemes Simulia Corp., Johnston, RI (US); Paul G. Bremner, Del Mar, CA (US)

(*) Notice: Subject to any disclaimer, the term of this patent is extended or adjusted under 35 U.S.C. 154(b) by 104 days.

(21) Appl. No.: 14/971,598

(22) Filed: Dec. 16, 2015

(65) Prior Publication Data

US 2016/0103167 A1  Apr. 14, 2016

Related U.S. Application Data

(63) Continuation of application No. PCT/US2014/043482, filed on Jun. 20, 2014, and a continuation of application No. PCT/US2014/043492, filed on Jun. 20, 2014, said application No. PCT/US2014/043482 is a
(Continued)

(51) Int. Cl.
*G01R 23/16* (2006.01)
*G01R 29/08* (2006.01)
*G01R 21/133* (2006.01)

*G06F 17/18* (2006.01)
*G01R 13/02* (2006.01)
*G01N 27/02* (2006.01)
(Continued)

(52) U.S. Cl.
CPC ............. *G01R 23/16* (2013.01); *G01N 27/02* (2013.01); *G01R 13/02* (2013.01); *G01R 21/133* (2013.01); *G01R 29/0814* (2013.01); *G01R 29/0892* (2013.01); *G01V 3/165* (2013.01); *G06F 17/18* (2013.01); *G06F 17/5018* (2013.01); *G01V 2210/6163* (2013.01)

(58) Field of Classification Search
None
See application file for complete search history.

(56) References Cited

U.S. PATENT DOCUMENTS 5,189,366 A    2/1993  Mayo
5,751,600 A    5/1998  Ochi et al.
(Continued)

OTHER PUBLICATIONS

Langley, Robin S. "A Reciprocity Approach for Computing the Response of Wiring Systems to Diffuse Electromagnetic Fields." IEEE Transactions on Electromagnetic Compatibility, vol. 52, No. 4, 2010, pp. 1041-1055., doi:10.1109/temc.2010.2068051.*
(Continued)

*Primary Examiner* — Joseph Schoenholtz
(74) *Attorney, Agent, or Firm* — Hamilton, Brook, Smith & Reynolds, P.C.

(57) ABSTRACT

Some embodiments include an apparatus for determining statistics of the current in various wiring systems exposed to diffuse electromagnetic fields. Other embodiments of related apparatuses and methods are also disclosed.

21 Claims, 10 Drawing Sheets

Related U.S. Application Data continuation-in-part of application No. 13/227,330, filed on Sep. 7, 2011, now Pat. No. 9,117,040, said application No. PCT/US2014/043492 is a continuation-in-part of application No. 13/227,330.

(60) Provisional application No. 61/838,099, filed on Jun. 21, 2013, provisional application No. 61/838,091, filed on Jun. 21, 2013, provisional application No. 61/474,367, filed on Apr. 12, 2011.

(51) Int. Cl.
*G01V 3/165* (2006.01)
*G06F 17/50* (2006.01)

(56) References Cited

U.S. PATENT DOCUMENTS

| | | | |
|---|---|---|---|
| 2003/0019291 | A1 | 1/2003 | Pchelnikov et al. |
| 2006/0279273 | A1 | 12/2006 | Kazama |
| 2008/0097730 | A1* | 4/2008 | Canning ............. G06F 17/5036 703/1 |
| 2008/0127756 | A1 | 6/2008 | Horton et al. |
| 2008/0136189 | A1 | 6/2008 | Qu et al. |
| 2008/0276207 | A1* | 11/2008 | Suaya ................. G06F 17/5009 716/106 |
| 2009/0167321 | A1 | 7/2009 | Krueger et al. |
| 2010/0125438 | A1 | 5/2010 | Audet |
| 2012/0010836 | A1 | 1/2012 | Shemesh et al. |
| 2012/0265464 | A1 | 10/2012 | Langley |
| 2014/0019050 | A1* | 1/2014 | Lambot ................... G01V 3/12 702/7 |

OTHER PUBLICATIONS

Tesche, F.M., and P.R. Barnes. "A Multiconductor Model for Determining the Response of Power Transmission and Distribution Lines to a High Altitude Electromagnetic Pulse (HEMP)." IEEE Transactions on Power Delivery, vol. 4, No. 3, 1989, pp. 1955-1964., doi:10.1109/61.32695.*

MIL-STD-1310H, Sep. 17, 2009.*

MIL DTL 24643B, Aug. 22, 2002.*

Langley, Robin S. "A Reciprocity Approach for Computing the Response of Wiring Systems to Diffuse Electromagnetic Fields." IEEE Transactions on Electromagnetic Compatibility, vol. 52, No. 4, 2010, pp. 1041-1055., doi:10.1109/temc.2010.206805.*

Drexler, Petr, and Pavel Fiala. "Methods for High-Power EM Pulse Measurement." IEEE Sensors Journal, vol. 7, No. 7, 2007, pp. 1006-1011., doi:10.1109/jsen.2007.896532.*

Langley, Robin S., "A Reciprocity Approach for Computing the Response of Wiring Systems to Diffuse Electromagnetic Fields", Nov. 17, 2010, IEEE Transactions on Electromagnetic Compatibility, vol. 52, No. 4, IEEE.

Langley, R. S., "On the Diffuse Field Reciprocity Relationship and Vibrational Energy Variance in a Random Subsystem at High Frequencies", Feb. 2007, Journal of Acoustic Society of America, Acoustic Society of America.

Shorter, P.J. et al., "On the Reciprocity Relationship Between Direct Field Radiation and Diffuse Reverberant Loading", Jan. 2005, Journal of Acoustic Society of America, Acoustic Society of America.

Andersen, J. Bach et al., "Room Electromagnetics", Apr. 2007, IEEE Antennas and Propagation Magazine, vol. 49, No. 2, IEEE.

Ishimaru, Akira et al., "Sommerfeld and Zenneck Wave Propagation for a Finely Conducting One-Dimensional Rough Surface", Sep. 2000, IEEE Transactions on Antennas and Propagation, vol. 48 No. 9, IEEE.

International Search Report and Written Opinion for PCT/US2014/043482, 14 pages, dated Oct. 10, 2014.

International Search Report and Written Opinion for PCT/US2014/043492, 11 pages, dated Oct. 30, 2014.

Non-Final Office for U.S. Appl. No. 14/971,652, entitled "Apparatus and Method for Determining Statistical Mean and Maximum Expected Variance of Electromagnetic Energy Transmission Between Coupled Cavities," dated Nov. 2, 2017.

Non-Final Office for U.S. Appl. No. 14/971,652, entitled "Apparatus and Method for Determining Statistical Mean and Maximum Expected Variance of Electromagnetic Energy Transmission Between Coupled Cavities," dated Mar. 9, 2017.

* cited by examiner

APPARATUS AND METHOD FOR DETERMINING STATISTICS OF ELECTRIC CURRENT IN AN ELECTRICAL SYSTEM EXPOSED TO DIFFUSE ELECTROMAGNETIC FIELDS

CROSS-REFERENCE TO RELATED APPLICATIONS

This application is a continuation application of International Patent Application No. PCT/US2014/043482, filed Jun. 20, 2014, and is a continuation application of International Patent Application No. PCT/US2014/043492, filed Jun. 20, 2014. International Patent Application No. PCT/US2014/043482 and International Patent Application No. PCT/US2014/043492 each claim the benefit of U.S. Provisional Application No. 61/838,091, filed Jun. 21, 2013, and U.S. Provisional Application No. 61/838,099, filed Jun. 21, 2013. Meanwhile, International Patent Application No. PCT/US2014/043482 and International Patent Application No. PCT/US2014/043492 each are a continuation-in-part application of U.S. patent application Ser. No. 13/227,330, filed Sep. 7, 2011, which claims priority from of U.S. Provisional Patent Application No. 61/474,367, filed Apr. 12, 2011. International Patent Application No. PCT/US2014/043482 and International Patent Application No. PCT/US2014/043492, U.S. Provisional Application No. 61/838,091, U.S. Provisional Application No. 61/838,099, U.S. patent application Ser. No. 13/227,330, and U.S. Provisional Patent Application No. 61/474,367 each are incorporated herein by reference in their entirety.

FIELD OF THE INVENTION

This invention relates generally to apparatuses and methods for modeling and analyzing electromagnetic fields in an electrical system, and relates more particularly to apparatuses and methods for determining statistics of electric current in the electrical system by modeling and analyzing the electromagnetic fields in the electrical system.

DESCRIPTION OF THE BACKGROUND

Many situations can exist in which electromagnetic fields can induce electric currents in an electrical system, such as, for example, an electrical system of a vehicle (e.g., an automobile, an aircraft, a ship, etc.) or an immobile structure (e.g., a building). For example, mobile phone transmitters, Bluetooth® transmitters, and electromagnetic pulse weapons are each potential sources of electromagnetic fields able to induce electric currents in the electrical system. These induced electric currents can potentially damage and/or interfere with the electrical system. Computationally analyzing electrical systems prior to implementation can permit electromagnetic fields in electrical systems to be modeled so that the electrical system can be designed to mitigate or eliminate formation of such induced electrical currents in order to protect the integrity of the electrical system. However, using a direct deterministic calculation to model the electromagnetic fields can be inefficient and/or less than realistic.

Accordingly, improved apparatuses and methods for modeling and analyzing electromagnetic fields in an electrical system are needed.

BRIEF DESCRIPTION OF THE DRAWINGS

To facilitate further description of the embodiments, the following drawings are provided in which.

Figure 1:
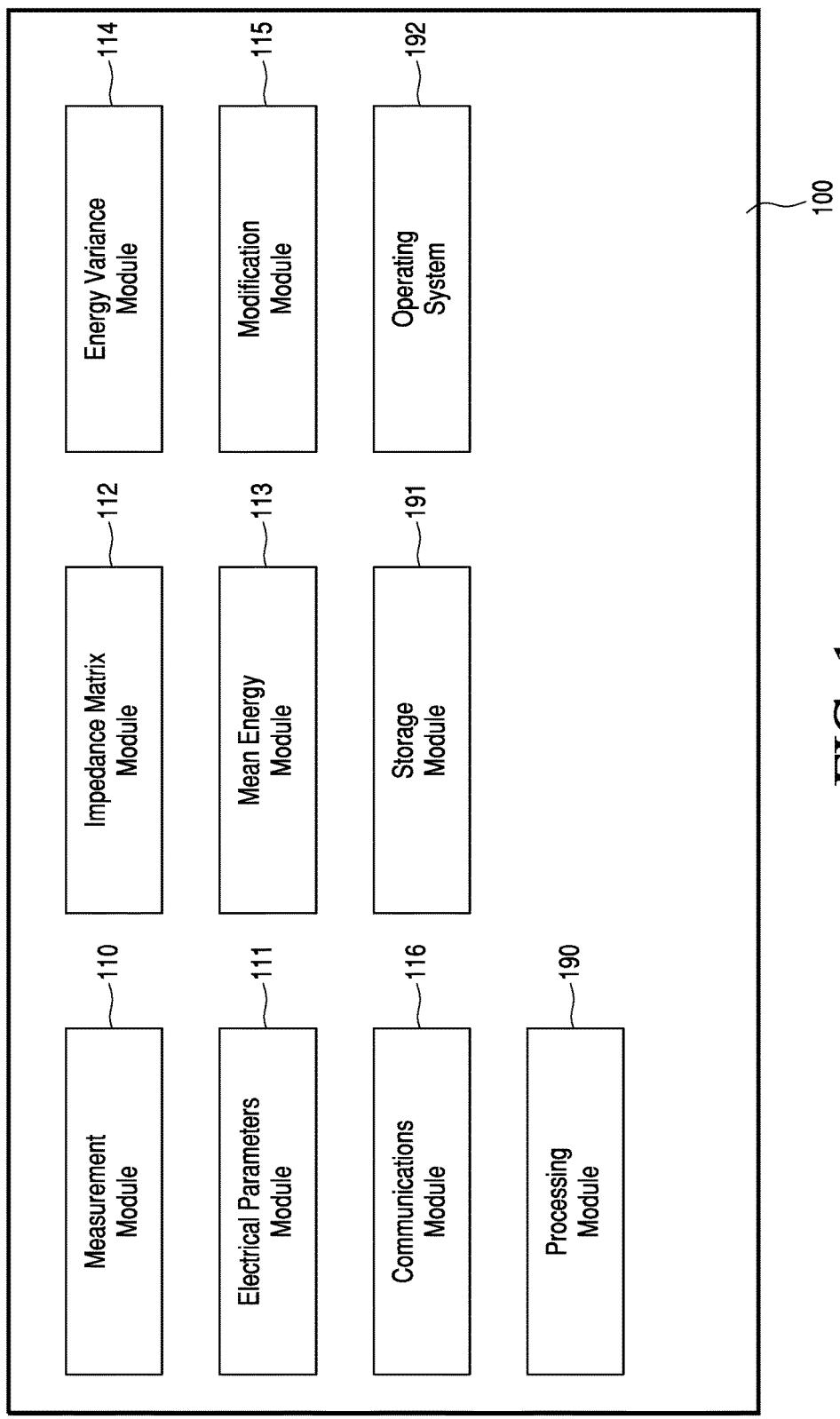
FIG. 1 illustrates a representative block diagram of an apparatus configured to determine (e.g., model and/or analyze) one or more electromagnetic fields in one or more conductive elements (e.g., wires) of an electrical system, according to an embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements or signals, electrically, mechanically and/or otherwise. Two or more electrical elements may be electrically coupled but not be mechanically or otherwise coupled; two or more mechanical elements may be mechanically coupled, but not be electrically or otherwise coupled; two or more electrical elements may be mechanically coupled, but not be electrically or otherwise coupled. Coupling may be for any length of time, e.g., permanent or semi-permanent or only for an instant.

"Electrical coupling" and the like should be broadly understood and include coupling involving any electrical signal, whether a power signal, a data signal, and/or other types or combinations of electrical signals. "Mechanical coupling" and the like should be broadly understood and include mechanical coupling of all types.

The absence of the word "removably," "removable," and the like near the word "coupled," and the like does not mean that the coupling, etc. in question is or is not removable.

DETAILED DESCRIPTION OF EXAMPLES OF EMBODIMENTS

Some embodiments include an apparatus configured to determine one or more electromagnetic fields in one or more conductive elements of an electrical system. The one or more electromagnetic fields can be caused by one or more electrical waves emitted by at least one electromagnetic wave creation element of the electrical system. Meanwhile, the apparatus comprises a processing module and a non-transitory memory storage module operable to store computer instructions configured to run on the processing module. Further, the computer instructions are configured to perform acts of: receiving two or more physical parameters of the one or more conductive elements; receiving one or more electrical parameters of the at least one electromagnetic wave creation element; determining at least one impedance matrix for the one or more conductive elements; determining a mean energy of the one or more electromagnetic fields in the one or more conductive elements; and determining an energy variance of the one or more electromagnetic fields in the one or more conductive elements.

Further embodiments include a method of determining one or more electromagnetic fields in one or more conductive elements of an electrical system. The one or more electromagnetic fields can be caused by one or more electrical waves emitted by at least one electromagnetic wave creation element of the electrical system. Meanwhile, the method can comprise: determining two or more physical parameters of the one or more conductive elements; determining one or more electrical parameters of the at least one electromagnetic wave creation element; executing one or more first computer instructions configured to determine at least one impedance matrix for the one or more conductive elements; executing one or more second computer instructions configured to determine a mean energy of the one or more electromagnetic fields in the one or more conductive elements; and executing one or more third computer instructions configured to determine an energy variance of the one or more electromagnetic fields in the one or more conductive elements. Further, the one or more first computer instructions, the one or more second computer instructions, and the one or more third computer instructions can be configured to run at a processing module and can be configured to be stored at a non-transitory memory storage module.

Other embodiments include a method of determining one or more electromagnetic fields in one or more wires of an electrical system. The one or more electromagnetic fields can be caused by one or more electrical waves emitted by at least one electromagnetic wave creation element of the electrical system. Meanwhile, the method can comprise: executing one or more first computer instructions configured to identify two or more physical parameters of the one or more wires; executing one or more second computer instructions configured to identify one or more electrical parameters of the at least one electromagnetic wave creation element; executing one or more third computer instructions configured to determine a mean energy of the one or more electromagnetic fields in the one or more wires; executing one or more fourth computer instructions configured to use the mean energy of the one or more electromagnetic fields in the one or more wires to determine one or more potential changes to at least one of (i) the one or more wires, (ii) a region surrounding the one or more wires, or (iii) the at least one electromagnetic wave creation element; and executing one or more fifth computer instructions configured to model the one or more potential changes. Further, the one or more first computer instructions, the one or more second computer instructions, the one or more third computer instructions, the one or more fourth computer instructions, and the one or more fifth computer instructions can be configured to run at a processing module and can be configured to be stored at a non-transitory memory storage module.

Some embodiments include a method of determining one or more electromagnetic fields in one or more conductive elements of an electrical system. The electromagnetic field(s) can be caused by one or more electrical waves emitted by at least one electromagnetic wave creation element of the electrical system. The method can comprise: determining two or more physical parameters of the one or more conductive elements; determining one or more electrical parameters of the at least one electromagnetic wave creation element; using a processing module to determine at least one impedance matrix for the one or more conductive elements; using the processing module to determine a mean energy of the one or more electromagnetic fields in the one or more conductive elements; and using the processing module to determine an energy variance of the one or more electromagnetic fields in the one or more conductive elements.

Further embodiments include an apparatus configured to use processing module to determine one or more electromagnetic fields in one or more conductive elements of an electrical system. The electromagnetic field(s) can be caused by one or more electrical waves emitted by at least one electromagnetic wave creation element of the electrical system. The apparatus comprises a measurement module, an electrical parameters module, an impedance matrix module, a mean energy module, and an energy variance module. The measurement module can be configured to run on the processing module and further configured to receive two or more physical parameters of the conductive element(s). Meanwhile, the electrical parameters module can be configured to run on the processing module and further configured to receive one or more electrical parameters of the electromagnetic wave creation element(s). Further, the impedance matrix module can be configured to run on the processing module and further configured to determine at least one impedance matrix for the conductive element(s). Further still, the mean energy module can be configured to run on the processing module and further configured to determine a mean energy of the electromagnetic field(s) in the conductive element(s). Also, the energy variance module can be configured to run on the processing module and further configured to determine an energy variance of the electromagnetic field(s) in the conductive element(s).

Other embodiments include a method of determining one or more electromagnetic fields in one or more wires of an electrical system. The electromagnetic field(s) can be caused by one or more electrical waves emitted by at least one electromagnetic wave creation element of the electrical system. The method can comprise: determining two or more physical parameters of the one or more wires; determining one or more electrical parameters of the at least one electromagnetic wave creation element; using a processing module to determine a mean energy of the one or more electromagnetic fields in the one or more wires; and using the mean energy of the one or more electromagnetic fields in the one or more wires to determine one or more potential changes to at least one of (i) the one or more wires, (ii) a region surrounding the one or more wires, or (iii) the at least one electromagnetic wave creation element.

As a preliminary matter, and as discussed in greater detail below, embodiments of the apparatuses and methods described herein can be operable to compute statistics of an electric current induced in a complex network (e.g., a bundle) of conductive elements (e.g., wires) subjected to one or more electromagnetic waves (e.g., diffuse electromagnetic waves).

Further, embodiments of the apparatuses and methods described herein can build upon the teachings of U.S. patent application Ser. No. 13/227,330. For example, U.S. patent application Ser. No. 13/227,330 describes a method for computing an electric current in a conductive element (e.g., wire) caused by diffuse electromagnetic waves in a cavity. The method includes calculating an impedance matrix of the conductive element (e.g., wire). Taking these concepts further, embodiments of the apparatuses and methods described herein can be operable to compute an impedance matrix for complex conductive element (e.g., wire) bundles and can implement these concepts in a variance of a cross-spectral matrix.

Likewise, U.S. patent application Ser. No. 13/227,330 also concerns an electrical system including two bare conductive elements (e.g., wires) that are spaced apart from each other. Embodiments of the apparatuses and methods described herein can be operable to model an arbitrary quantity of bare conductive elements (e.g., wires) of an electrical system having arbitrary spacing between the conductive elements (e.g., wires), and can be extended to model the conductive elements even when having multi-layer coatings around the conductive elements. Further, conductive elements (e.g., wires) in the vicinity of a wall and/or conductive elements that are connected in a network can also be modeled by embodiments of the apparatuses and methods described herein. This modeling allows for a determination of various properties of the electric currents and/or electromagnetic fields in the conductive elements (e.g., wires), a likelihood that the electromagnetic waves would damage electrical systems including the conductive elements, and of potential changes to the electrical systems or the environment that may be implemented to mitigate or eliminate damage to and/or interference with the electrical system.

As noted in the description of the background above, electric currents induced in an electrical system by electromagnetic waves can potentially damage the electrical system. A characteristic of this type of problem is that a source of electromagnetic excitation can produce an electromagnetic field inside a cavity, which can then damage and/or interfere with the electrical system. In many examples, a frequency of the electromagnetic excitation is relatively high, in that the electromagnetic wavelength is short in comparison to the dimensions of the cavity. For example, a typical mobile phone transmitter can produce electromagnetic excitation at around 2 Gigahertz (GHz) and a wavelength of 15 centimeters (cm), meaning that an electromagnetic field produced within a typical cabin of a vehicle (e.g., an automobile, an aircraft, a ship, etc.) will have a spatially complex distribution.

Theoretically, an electromagnetic field in an electrical system can be predicted numerically by solving Maxwell's equations for the electrical system, using either a finite element analysis or the finite difference analysis to capture the detailed spatial distribution of the electromagnetic fields. However, to calculate the electromagnetic fields using such a deterministic analysis can require a large amount of computing power and a large amount of storage. That is, a deterministic analysis can require computational analysis of many grid points (e.g., millions of grid points). In one example, fifteen million grid points (i.e., degrees of freedom) were used to calculate the electromagnetic fields for a single cavity in an exemplary automobile.

Another feature of short wavelength electromagnetic excitation is that the response of an electrical system can be very sensitive to small changes. For example, moving a wire harness by several centimeters can significantly change the resulting electromagnetic fields in an electrical system. Accordingly, when using a deterministic model, it may be necessary to completely remodel an electrical system when any small change is made to the electrical system.

In view of the limitations of deterministic analysis, notably, it has been determined that a short wavelength electromagnetic field inside a cavity of a vehicle or immobile structure can be well approximated as an ideal diffuse wave field. Taking advantage of this determination, the apparatuses and methods described herein can approximate the electromagnetic waves in an electrical system more efficiently than a direct deterministic analysis by analyzing the electromagnetic waves as ideal diffuse wave fields, while also being more realistic from a statistical point of view.

Turning now to the drawings, FIG. 1 illustrates a representative block diagram of an apparatus 100 configured to determine (e.g., model and/or analyze) one or more electromagnetic fields in one or more conductive elements (e.g., wires) of an electrical system, according to an embodiment. The electromagnetic field(s) can be caused by one or more electrical waves emitted by at least one electromagnetic wave creation element of the electrical system. Apparatus 100 is merely exemplary and is not limited to the embodiments presented herein. Apparatus 100 can be employed in many different embodiments or examples not specifically depicted or described herein. In some embodiments, the electrical system can be similar or identical to an electrical system 200 (FIG. 2), as described in greater detail below.

Figure 2:
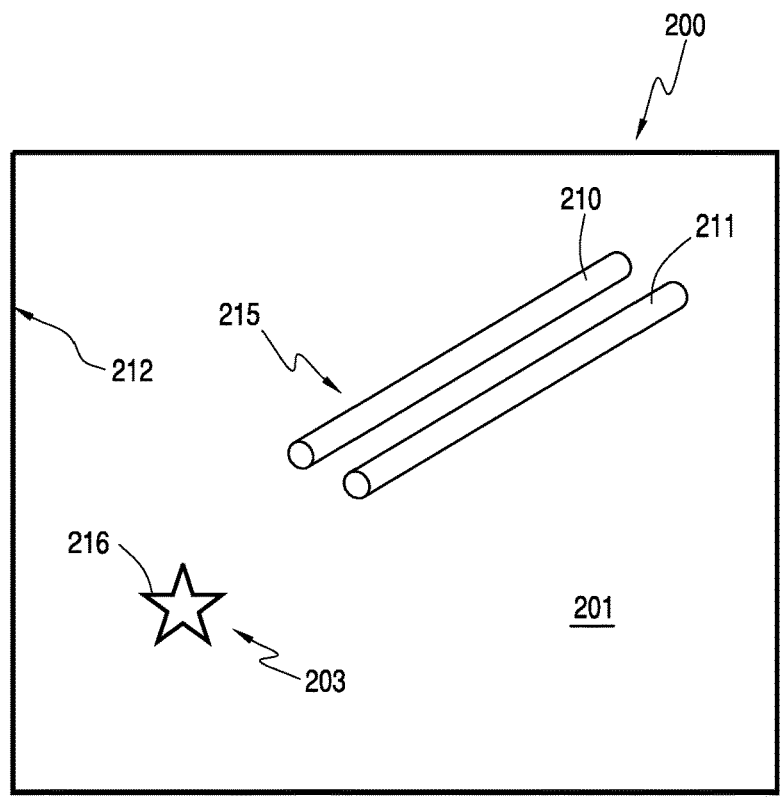
FIG. 2 illustrates a representative block diagram of an exemplary electrical system, according to an embodiment.

Turning ahead briefly in the drawings, FIG. 2 illustrates a representative block diagram of an exemplary electrical system 200, according to an embodiment. Electrical system 200 can comprise at least one electromagnetic wave creation element 203 (e.g., an electromagnetic wave creation element 216), one or more conductive elements 215 (e.g., a conductive element 210 and/or a conductive element 211), and a cavity 201. Further, electrical system 200 and/or cavity 201 can comprise one or more walls 212.

In many embodiments, conductive element(s) 215 (e.g., a conductive element 210 and/or a conductive element 211) can comprise one or more wires. Although FIG. 2 illustrates conductive element(s) 215 as comprising only two conductive elements, in other embodiments, conductive element(s) 215 can comprise any suitable quantity of conductive elements (e.g., wires).

In some embodiments, conductive element(s) 215 (e.g., a conductive element 210 and/or a conductive element 211) can comprise any suitable electrically conductive materials (e.g., at a core of each of conductive element(s) 215) and/or can comprise one or more coatings (e.g., shielding layers or other dielectric coatings), such as, for example, around (e.g., enclosing) the core of conductive element(s) 215. Further, conductive element(s) 215 (e.g., a conductive element 210 and/or a conductive element 211) can be spaced together or spaced apart. One or more conductive elements of conductive element(s) 215 (e.g., a conductive element 210 and/or a conductive element 211) can be similar or different from each other. For example, conductive element(s) 215 (e.g., a conductive element 210 and/or a conductive element 211) can comprise the same or different materials, the same or different coatings, the same or different spacing, etc. Further, in some embodiments, conductive element(s) 215 (e.g., a conductive element 210 and/or a conductive element 211) can share the same coatings or can be coated separately. In various embodiments, conductive element(s) 215 (e.g., a conductive element 210 and/or a conductive element 211) can be coupled with one or more electrical components as part of one or more electrical networks. Exemplary electrical components can comprise any suitable device(s) (e.g., appliances, etc.) configured to be electrically coupled with conductive element(s) 215 (e.g., a conductive element 210 and/or a conductive element 211).

In many embodiments, electromagnetic wave creation element(s) 203 (e.g., electromagnetic wave creation element 216) can comprise one or more sources of electromagnetic radiation. That is, electromagnetic wave creation element(s) 203 (e.g., electromagnetic wave creation element 216) can be configured to emit electrical waves. Exemplary electromagnetic wave creation element(s) 203 (e.g., electromagnetic wave creation element 216) can comprise a mobile communication device (e.g., a mobile phone transmitter, a Bluetooth® transmitter, etc.), an electromagnetic pulse weapon, lightning, and/or any other electromagnetic source suitably configured to emit electrical waves.

In many embodiments, one or more of electromagnetic wave creation element(s) 203 (e.g., electromagnetic wave creation element 216) and conductive element(s) 215 (e.g., conductive element 210 and/or conductive element 211) can be located inside of cavity 201. Further, in some embodiments, one or more of electromagnetic wave creation element(s) 203 can be located inside of cavity 201 and one or more of conductive element(s) 215 (e.g., conductive element 210 and/or conductive element 211) can be located inside of one of walls 212.

In some examples, cavity 201 can comprise a cabin or a compartment of a vehicle (e.g., an automobile, a ship, an aircraft, etc.). In other examples, cavity 201 can comprise a room or compartment of an immobile structure (e.g., a commercial building or a house).

Turning now back to FIG. 1, in many embodiments, apparatus 100 can refer to an electromagnetic field modeling apparatus (i.e. a electromagnetic field modeling system). In various embodiments, apparatus 100 can comprise a computer system. The computer system can be similar or identical to computer system 1200 (FIG. 12), as described below.

Accordingly, in these or other embodiments, apparatus 100 can comprise a processing module 190, a communications module 116, a storage module 191, and an operating system module 192. Further, apparatus 100 can comprise a measurement module 110, an electrical parameters module 111, an impedance matrix module 112, a mean energy module 113, an energy variance module 114, and a modification module 115. In some embodiments, part or all of processing module 190, communications module 116, storage module 191, and/or operating system module 192 can be omitted.

In implementation, processing module 190 can comprise one or more processors. As used herein, a "processor" can mean any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions (e.g., running computer software).

Meanwhile, storage module 191 can comprise one or more non-volatile computer memory storage devices configured to store computer software (e.g., computer instructions) and/or data (e.g., data related to apparatus 100 and/or electrical system 200 (FIG. 2)) on a temporary and/or permanent basis for use by apparatus 100 and/or processing module 190. Notably, apparatus 100 can also include one or more volatile computer memory storage devices.

In many embodiments, at least part of measurement module 110, electrical parameters module 111, impedance matrix module 112, mean energy module 113, energy variance module 114, modification module 115, communications module 116, and/or operating system module 192 can be implemented as computer software. Accordingly, in these or other embodiments, at least part of measurement module 110, electrical parameters module 111, impedance matrix module 112, mean energy module 113, energy variance module 114, modification module 115, communications module 116, and/or operating system module 192 can be configured to run at processing module 190 and/or to be stored at storage module 191. In some embodiments, at least part of measurement module 110, electrical parameters module 111, impedance matrix module 112, mean energy module 113, energy variance module 114, modification module 115, communications module 116, and/or operating system module 192 can also be configured to be stored at the volatile computer memory storage devices of apparatus 100 as may be necessary to performed the desired functions of apparatus 100.

Communications module 116 can be configured to permit communication between processing module 190 and storage module 191, and between apparatus 100 and one or more users of apparatus 100. For example, communications module 116 can permit processing module 190 to call computer software (e.g., at least part of measurement module 110, electrical parameters module 111, impedance matrix module 112, mean energy module 113, energy variance module 114, modification module 115, communications module 116, and/or operating system module 192) stored at storage module 191 and/or data stored at storage module 191 for operation of apparatus 100. Further, communications module 116 can permit data calculated by processing module 190 to be communicated to storage module 191 for storage. Further still, communications module 116 can permit any user(s) of apparatus 100 to provide inputs (e.g., commands) to processing module 190 and/or storage module 191, and can provide data calculated by processing module 190 to be output to the user(s). The input(s) can be provided by any suitable input mechanism(s) (e.g., a keyboard, mouse, etc.) and the output(s) can be provided at any suitable output mechanism(s) (e.g., displays, speakers, etc.). Notably, the input and/or output mechanism(s) can be integral with apparatus 100 or can be partially or entirely part of another apparatus, such as, for example, another computer system.

Although at least part of communications module 116 can be implemented as computer software, at least part of communications module 116 can also be implemented as any suitable hardware configured to perform the desired communication for apparatus 100. For example, communications module 116 can comprise (a) one or more transmission components configured to provide wired communication (e.g., one or more data buses, such as, for example, universal serial bus(es); one or more networking cables, such as, for example, coaxial cable(s), optical fiber cable(s), and/or twisted pair cable(s); any other suitable data cable, etc.) and/or (b) one or more transmission components configured to provide wireless communication (e.g., one or more radio transceivers, one or more infrared transceivers, etc.). Also, communications module 116 can comprise one or more networking components (e.g., modulator-demodulator components, gateway components, etc.). Further, communications module 116 can be configured to operate using any one or any combination of wired and/or wireless communication network topologies (e.g., ring, line, tree, bus, mesh, star, daisy chain, hybrid, etc.) and/or protocols (e.g., personal area network (PAN) protocol(s), local area network (LAN) protocol(s), wide area network (WAN) protocol(s), cellular network protocol(s), Powerline network protocol(s), etc.). Exemplary PAN protocol(s) can comprise Bluetooth, Zigbee, Wireless Universal Serial Bus (USB), Z-Wave, etc.; exemplary LAN and/or WAN protocol(s) can comprise Institute of Electrical and Electronic Engineers (IEEE) 802.3, IEEE 802.11, etc.; and exemplary wireless cellular network protocol(s) can comprise Global System for Mobile Communications (GSM), General Packet Radio Service (GPRS), Code Division Multiple Access (CDMA), Evolution-Data Optimized (EV-DO), Enhanced Data Rates for GSM Evolution (EDGE), 3GSM, Digital Enhanced Cordless Telecommunications (DECT), Digital AMPS (IS-136/Time Division Multiple Access (TDMA)), Integrated Digital Enhanced Network (iDEN), etc. The software and/or hardware of communications module 116 can be dependent on the network topologies and/or protocols in use, and vice versa.

In various embodiments, operating system 192 can comprise computer software configured to manage the hardware and computer software resources of a computer and/or a computer network. Operating system 192 can perform basic tasks such as, for example, controlling and allocating memory, prioritizing the processing of instructions, controlling input and output devices, facilitating networking, and managing files. Examples of common operating systems for a computer include Microsoft® Windows, Mac® operating system (OS), UNIX® OS, and Linux® OS.

In some embodiments, when apparatus 100 comprises a computer system, the computer system can comprise a single computer, a single server, or a cluster or collection of servers. Typically, a cluster or collection of servers can be used when the demands by apparatus 100 are beyond the reasonable capability of a single computer or a single server. In many embodiments, the servers in the cluster or collection of servers are interchangeable from the perspective of the users.

Meanwhile, although processing module 190, communications module 116, storage module 191, operating system module 192, measurement module 110, electrical parameters module 111, impedance matrix module 112, mean energy module 113, energy variance module 114, and/or modification module 115 are described herein generally as being located at part of a single computer or server, in many embodiments, parts of any of processing module 190, communications module 116, storage module 191, operating system module 192, measurement module 110, electrical parameters module 111, impedance matrix module 112, mean energy module 113, energy variance module 114, and/or modification module 115 may be spread between and/or possibly overlap at multiple servers when the computer system of apparatus 100 comprises a cluster of collection of servers. For example, the computer system of apparatus 100 can comprise a first server comprising a first portion of one or more of processing module 190, communications module 116, storage module 191, operating system module 192, measurement module 110, electrical parameters module 111, impedance matrix module 112, mean energy module 113, energy variance module 114, and/or modification module 115. Meanwhile, one or more second servers can comprise a second, possibly overlapping, portion of processing module 190, communications module 116, storage module 191, operating system module 192, measurement module 110, electrical parameters module 111, impedance matrix module 112, mean energy module 113, energy variance module 114, and/or modification module 115.

In operation, measurement module 110 can be configured to receive one or more (e.g., two or more) physical parameters of the conductive element(s) of the electrical system. In these or other embodiments, the physical parameters of the conductive element(s) of the electrical system can comprise: (a) one or more physical properties of the conductive element(s) of the electrical system; (b) one or more locations of the conductive element(s) relative to one or more walls of the electrical system; (c) one or more properties of one or more coatings on the conductive element(s) of the electrical system; (d) one or more properties of electrical components coupled with the conductive element(s) of the electrical system as part of one or more electrical networks. Further in these or other embodiments, the one or more physical properties of the conductive element(s) of the electrical system can comprise: (a) one or more diameters of the conductive element(s) of the electrical system; (b) one or more lengths of the conductive element(s) of the electrical system; or (c) one or more material properties of the conductive element(s) of the electrical system. In many embodiments, measurement module 110 can also be configured to receive one or more physical parameters (e.g., dimensions) of one or more cavities and/or one or more walls of the electrical system.

In some embodiments, and for some physical parameters of the conductive element(s) of the electrical system, apparatus 100 can receive the physical parameters of the conductive element(s) of the electrical system through communication with one or more sensors configured to measure the physical parameter(s) or a user of apparatus 100 can provide the physical parameters by manual entry. When the user manually enters the physical parameter(s), the user may physically measure the physical parameters (e.g., using sensors and/or measurement devices, such as, for example, calipers, tape measures, etc.) and/or use reference materials related to the electrical system (e.g., schematics, blueprints, architectural drawings, etc.) to obtain the physical parameters.

Further, in many embodiments, electrical parameters module 111 can be configured to receive one or more electrical parameters of the electromagnetic wave creation element(s) of the electrical system. In these or other embodiments, the electrical parameters of the electromagnetic wave creation element(s) can comprise (a) one or more electric powers of electromagnetic waves emitted by the electromagnetic wave creation element(s) at one or more frequencies and/or (b) the one or more frequencies of the electromagnetic waves. Electrical parameters module 111 can receive the electrical parameters of the electromagnetic wave creation element(s) of the electrical system through communication with one or more sensors configured to measure the electrical parameter(s) or a user of apparatus 100 can provide the electrical parameters by manual entry. When the user manually enters the electrical parameter(s), the user may physically measure the electric power(s) and/or frequencies of the electromagnetic waves emitted by the electromagnetic wave creation element(s) (e.g., using sensors) and/or use reference materials related to the electromagnetic wave creation element(s) to obtain the power(s) and/or frequencies.

In many embodiments, when measurement module 110 and/or electrical parameters module 111 receive the physical properties of the conductive element(s) of the electrical system and/or the electrical parameter(s) of the electromagnetic wave creation element(s) of the electrical system, respectively, the physical properties and/or the electrical parameter(s) can be stored at storage module 191. Meanwhile, impedance matrix module 112, mean energy module 113, energy variance module 114, and/or modification module 115 can access the physical properties and/or the electrical parameter(s) directly or as stored at storage module 191 as necessary to perform their functionality.

Meanwhile, in further operation, impedance matrix module 112 can be configured to determine (e.g., calculate) at least one impedance matrix for the conductive element(s) of the electrical system (e.g., each conductive element of the conductive element(s) of the electrical system); mean energy module 113 can be configured to determine (e.g., calculate) a mean energy of the electromagnetic field(s) in the conductive element(s) (e.g., each conductive element of the conductive element(s) of the electrical system); and/or energy variance module 114 can be configured to determine (e.g., calculate) an energy variance of the electromagnetic field(s) in the conductive element(s) (e.g., each conductive element of the conductive element(s) of the electrical system).

Notably, the particular manner of operation of impedance matrix module 112, mean energy module 113, and energy variance module 114 can depend on the complexity of the electrical system, as discussed below. These varying manners of operation of impedance matrix module 112, mean energy module 113, and energy variance module 114 are discussed below. As an introductory matter, to aid in general understanding, details are provided discussing the relevant functionality of impedance matrix module 112, mean energy module 113, and energy variance module 114 as applicable for each in the context of a single conductive element (e.g., a single wire) of an electrical system in a diffuse electromagnetic field. Then, additional details are provided to discuss the relevant functionality of impedance matrix module 112, mean energy module 113, and energy variance module 114 as modified to accommodate multiple conductive elements having arbitrary spacing, having shielding and other arbitrary dielectric coatings, being located in the vicinity of a conducting wall or cavity surface, being bundled with different shielding layers, and being coupled by electrical components into one or more electrical networks.

Figure 3:
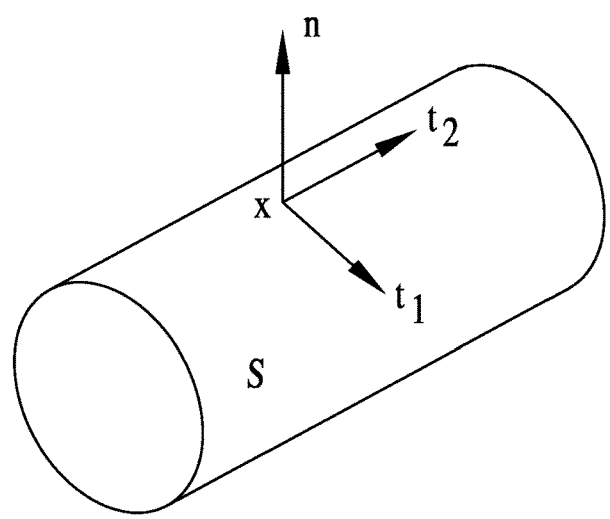
FIG. 3 illustrates an exemplary bounding surface S bounding an exemplary arbitrary region R.

To begin with, the concept of a surface impedance matrix is introduced. In particular, given an arbitrary region R in which Maxwell's equations apply, bounding surface S can refer to a surface bounding arbitrary region R. The tangential components of the electric and magnetic fields over bounding surface S are each described by a set of N generalized coordinates, respectively $e_j$ and $h_j$ for $j=1, 2, \ldots N$, which form the entries of two column vectors e and h. The relationship between the generalized coordinates and the tangential field components at some particular spatial point x on bounding surface S can be achieved via a set of shape functions so that, for example, the two tangential components of the tangential magnetic field can be written as $$H(x) = \begin{pmatrix} H_1(x) \\ H_2(x) \end{pmatrix} = \begin{pmatrix} f_1^T(x) \\ f_2^T(x) \end{pmatrix} h, \qquad (1)$$

where the column vectors $f_j(x)$ contain prescribed shape functions. FIG. 3 illustrates an exemplary bounding surface S bounding an exemplary arbitrary region R.

The prescribed shape functions may be locally acting (as in a finite element mesh) or globally extended over bounding surface S. If the surface tangential magnetic field is specified as a boundary condition to Maxwell's equations, and there are no other excitation sources within arbitrary region R, then Maxwell's equations can be solved to yield the complete electromagnetic field within arbitrary region R and the tangential electric field on bounding surface S.

The relationship between the specified surface magnetic field h and the resulting surface electric field e can be written in the form $$Zh=e, \qquad (2)$$

where Z is defined as the surface impedance matrix. In Equation (2), and all equations that follow, the electromagnetic field is taken to vary harmonically in time at frequency $\omega$, so that the surface electric field e and the specified surface magnetic field h represent complex amplitudes and further, the magnetic field, for example, at some time t has the form $Re\{h \exp(-i\omega t)\}$. The generalized coordinates are taken to be scaled and ordered so that the power radiated by bounding surface S into arbitrary region R is given by the scalar product h.e, corresponding to the integral over bounding surface S of the normal component of the Poynting vector. Given that the surface electric field e and the specified surface magnetic field h are taken to vary harmonically in time, the time average of the power radiated can be written in the form $$P=(\tfrac{1}{2})Re\{h^{*T}e\}=(\tfrac{1}{2})h^{*T}Z_H h, \qquad (3)$$

and such that $$Z_H = (1/2)(Z^{*T} + Z), \quad (4)$$

where $Z_H$ is the Hermitian part of the surface impedance matrix Z.

The concept of the surface impedance matrix introduced in Equations (1)-(4) can be applied to the analysis of an electrical element in a reverberant cavity, where arbitrary region R represents the electrical element. The electrical element can be similar or identical to any of conductive element(s) 215 (e.g., conductive element 210 and/or conductive element 211) of FIG. 2.

For example, given that bounding surface S lies within a reverberant cavity, two impedance matrices can be associated with bounding surface S. The first impedance matrix can be provided by solving Maxwell's equations within the electrical element. The second impedance matrix can be provided by solving Maxwell's equations within the reverberant cavity, where bounding surface S is treated as a boundary to the volume of the reverberant cavity.

The relationship between the specified surface magnetic field h and the resulting surface electric field e of the reverberant cavity can be written in the form $$Z_{cav} h = e, \quad (5)$$

where $Z_{cav}$ is the impedance matrix of the reverberant cavity. Because the cavity is reverberant, the solution of Maxwell's equations within the reverberant cavity can be numerically intensive. Accordingly, impedance matrix of the reverberant cavity $Z_{cav}$ can be very sensitive to changes in the cavity properties and also to changes in the location and shape of the bounding surface S. These issues can be highlighted by writing the impedance matrix in the form $$Z_{cav} = Z_D + Z_{rev} \quad (6)$$

where $Z_D$ is the impedance matrix associated with radiation from the bounding surface S into an infinitely extended region, and $Z_{rev}$ is the modification to this result arising from the finite cavity size. For Equation (6), impedance matrix $Z_D$ can be robust to changes in bounding surface S while impedance matrix $Z_{rev}$ can include the sensitivities associated with reverberation within the cavity. With this notation Equation (5) can be re-expressed in the forms $$Z_D h = e - e_b, \quad e_b = Z_{rev} h, \quad (7,8)$$

where $e_b$ can be viewed as an excitation term arising from reverberation within the cavity.

In some examples, Equation (7) can be derived in an alternative manner wherein the impedance relation on bounding surface S can be written in the form $$Z_D (h - h_{inc}) = e - e_{inc}. \quad (9)$$

such that $h_{inc}$ and $e_{inc}$ are the surface electric and magnetic fields, respectively, arising from reverberation within the cavity, which would be zero in a cavity of infinite volume. It follows that Equation (8) then yields $$Z_D h = e - e_b, \quad e_b = e_{inc} - Z_D h_{inc}. \quad (10,11)$$

Equations (7) and (10) are completely equivalent, with $e_b$ representing an excitation on bounding surface S arising from reverberation within the cavity. Equation (10) is simply an algebraic variant of Equation (5) but Equation (10) permits additional information to be derived regarding $e_b$. This information can be determined by application of the diffuse-field reciprocity principle. The diffuse-field reciprocity principle provides that a loading applied (e.g., an induced electric field) by an electromagnetic wave field within a reverberant cavity on an electrical element can be expressed in terms of the energy in the electromagnetic wave field and the radiation properties of the electrical element (i.e., the way in which the electrical element would radiate into the reverberant cavity, were the reverberant cavity infinitely extended). A non-patent reference R. S. Langley, *A Reciprocity Approach for Computing the Response of Wiring Systems to Diffuse Electromagnetic Fields*, IEEE Transactions on Electromagnetic Compatibility, vol. 52, pp. 1041-1055 (2010) provides additional information related to the diffuse-field reciprocity principle, and is incorporated herein by reference.

In the present context the principle states that $$E[e_b e_b^{*T}] = \left(\frac{4U}{\pi v}\right) Z_{DH}. \quad (12)$$

The expectation operator E[ ] on the left hand side of Equation (12) represents an average taken over an ensemble of random systems, generated by random changes in the position and shape of bounding surface S and also by random changes in the reverberant cavity (e.g., a change in position of a mode stirring device). On the right hand side of Equation (12), $Z_{DH}$ is the Hermitian part of the impedance matrix $Z_D$ (corresponding to radiation into an infinite domain), U is the electromagnetic energy of the cavity, and v is the modal density of the cavity (e.g., the average number of resonances in a unit frequency band). Electromagnetic energy of the cavity U and modal density of the cavity v are given by $$U = (1/2) V \varepsilon E[|E|^2], \quad v = \frac{V \omega^2}{\pi^2 c^3}, \quad (13, 14)$$

where V is the cavity volume, E is the electric field in the cavity, $\varepsilon$ is the permittivity, and c is the speed of light. As discussed below, Equation (12) provides an efficient solution to electromagnetic problems involving reverberant fields.

As noted above prior to Equation (5), an impedance matrix associated with bounding surface S as well as for the reverberant cavity can be calculated. The result of calculating the impedance matrix within bounding surface S can be written in the form $$Z_C h = -e + e_{app}, \quad (15)$$

where the sign convention on e has been taken to make radiation into the reverberant cavity positive and radiation into electrical element negative, and the additional term $e_{app}$ has been included to allow for any excitation applied directly to the electrical element, such as an applied voltage. Equations (10) and (15) can be combined to yield $$(Z_C + Z_D) h = Z_T h = e_{app} - e_b, \quad (16)$$

where $Z_T$ is the sum of the interior and exterior impedance matrices associated with bounding surface S. The solution to Equation (16) can be written in the form $$h = h_0 - Z_T^{-1} e_b, \quad h_0 = Z_T^{-1} e_{app}, \quad (17,18)$$

where $h_0$ is the solution that would be obtained in the absence of reverberation within the reverberating cavity.

Implementing Equations (1)-(18), it is possible to calculate the response of the reverberant cavity and the electrical element to an applied excitation source $e_{app}$. The response of the reverberant cavity can be obtained by considering power balance with the reverberant cavity, and the resulting reverberant cavity energy can be used to calculate a response of the electrical element. To consider power balance within the reverberant cavity, note that the ensemble average power radiated by the specific surface magnetic field h into the cavity follows from equation (10) as $$P_{in} = (1/2) E[h^{*T} Z_{DH} h] + (1/2) E[Re\{h^{*T} e_b\}]. \quad (19)$$

It then follows from Equation (17) that $$P_{in} = (1/2) E[h_0^{*T} Z_{DH} h_0] + (1/2) E[e_b^{*T} Z_T^{-T} Z_{DH} Z_T^{-1} e_b] - (1/2) E[e_b^{*T} (Z_T^{-1})_H e_b], \quad (20)$$

where it has been assumed that $E[e_b]=0$ (i.e., fluctuations in the surface fields due to reverberation are unbiased and therefore have zero mean). The second term on the left hand side of Equation (20) can be re-expressed by noting the following relation between the impedance matrices:

$$Z_T^{-T*} Z_{DH} Z_T^{-1} = Z_T^{-T*} Z_{TH} Z_T^{-1} - Z_T^{-T*} Z_{CH} Z_T^{-1} = (Z_T^{-1})_H - Z_T^{-T*} Z_{CH} Z_T^{-1}. \quad (21)$$

Equations (12), (20) and (21) then yield $$P_{in} = (1/2) E[h_0^{*T} Z_{DH} h_0] - \omega Q_d^{-1} U, \quad (22)$$

where $$\omega Q_d^{-1} = \left(\frac{2}{\pi \nu}\right) Tr[Z_T^{-T*} Z_{CH} Z_T^{-1} Z_{DH}], \quad (23)$$

and Tr[A] represents the trace of the matrix A. Now power balance for the cavity can be written as $$\omega Q^{-1} U = P_{in} + P_{add}, \quad (24)$$

where Q is the cavity loss factor (in the absence of the electrical element), and $P_{add}$ represents the power input from any additional excitation source (e.g., an aperture in the reverberant cavity). Equations (22) and (24) then yield $$\omega(Q^{-1} + Q_d^{-1}) U = P_{add} + (1/2) E[h_0^{*T} Z_{DH} h_0]. \quad (25)$$

It follows from Equation (25) that $Q_d$ can be identified as an addition to the cavity loss factor arising from the presence of the electrical element. Given the cavity energy from Equation (25), Equations (12) and (16) can be used to express the ensemble variance matrix of the surface magnetic field in the form $$E[hh^{*T}] = Z_T^{-1} \left\{ E[e_{app} e_{app}^{*T}] + \left(\frac{4U}{\pi \nu}\right) Z_{DH} \right\} Z_T^{-T*}. \quad (26)$$

Meanwhile, using Equations (25) and (26) with $h_0$ defined by Equation (18), the response of the reverberant cavity and electrical element to an excitation source can be calculated by: (i) calculating impedance matrix $Z_C$ within the electrical element, (ii) calculating the impedance matrix $Z_T$ associated with electric radiation into infinite space, and (iii) applying Equations (25) and (26). Advantageously, using this approach, it can be unnecessary to solve Maxwell's equations within the reverberating cavity, or to otherwise compute the detailed modes and/or impedance of the reverberating cavity, and moreover it can immediately yield statistically averaged results for the response of the electrical element.

The analysis leading to Equation (26) can be extended to yield the ensemble variance of the cross-spectral matrix $hh^{*T}$ in the form $$Var[hh^{*T}] = \frac{8U}{\pi \nu} (Z_T^{-1} E[e_{app} e_{app}^{*T}] Z_T^{-*T})_{ij} (Z_T^{-1} Z_{DH} Z_T^{-*T})_{ij} + 16 \left(\frac{2Var[U] + U^2}{\pi^2 \nu^2}\right) (Z_T^{-1} Z_{DH} Z_T^{-*T})_{ij} (Z_T^{-1} Z_{DH} Z_T^{-*T})_{ij}. \quad (27)$$

Given the ensemble mean and variance values yielded by Equations (26) and (27), the statistical distribution of any entry of the cross spectral matrix can be found by adopting a two parameter distribution, such as, for example, a lognormal distribution.

Accordingly, in many embodiments, impedance matrix module 112, mean energy module 113, and energy variance module 114 can apply the foregoing calculations to perform their respective functions. For example, in determining at least one impedance matrix for the conductive element(s) of the electrical system (e.g., each conductive element of the conductive element(s) of the electrical system), impedance matrix module 112 can calculate impedance matrix $Z_C$ and impedance matrix $Z_T$ for the conductive element(s) of the electrical system (e.g., each conductive element of the conductive element(s) of the electrical system). Meanwhile, mean energy module 113 can determine (e.g., calculate) a mean energy of the electromagnetic field(s) in the conductive element(s) (e.g., each conductive element of the conductive element(s) of the electrical system) using the mean squared current provided by Equation (26); and/or energy variance module 114 can determine (e.g., calculate) an energy variance of the electromagnetic field(s) in the conductive element(s) (e.g., each conductive element of the conductive element(s) of the electrical system) using the variance of the current cross-spectral matrix provided by Equation (27). A non-patent reference J. A. Stratton, *Electromagnetic Theory*, McGraw-Hill Book Company, New York and London (1941) provides additional information related to determining electric and magnetic fields in a conductive element, and is incorporated herein by reference.

Now, with having established the foregoing basic functionality of impedance matrix module 112, mean energy module 113, and energy variance module 114, the following discussion expands on these principles to cover more complex electrical systems. Accordingly, impedance matrix module 112, mean energy module 113, and energy variance module 114 can further be configured to apply these expanded principles in performing their respective functionality.

For example, the principles discussed with respect to Equations (1)-(27) can be applied to electrical systems comprising multiple conductive elements having arbitrary spacing. In many examples, the conductive elements can be similar or identical to conductive element(s) 215. As evident from the previous discussion of Equations (1)-(27), one or more impedance matrices for the electrical system can be determined. Although in some embodiments, the impedance matrices can be determined by using the method of moments, in many embodiments, a Fourier transform technique can be implemented. Assuming all spatial dependencies have the form $exp(ik_3 x_3)$ where the coordinate $x_3$ runs along the conductive elements and $k_3$ is a prescribed wavenumber extending in the direction of $x_3$, a circumferential magnetic field and an axial electric field on a surface of each conductive element can be assumed to be constant around a circumference of the conductive element, and the solution to Maxwell's equations in an infinite domain surrounding the electrical elements can be expressed in terms of an axisymmetric cylindrical transverse magnetic wave centered on each conductive element. More generally, both transverse magnetic and transverse electric waves can be included by making an extension to the methodology described as follows.

For a generic transverse magnetic formulation, the components of the electric and magnetic field can be:

$$E_Z \neq 0$$

$$E_\theta = 0$$

$$H_Z = 0$$

$$H_\theta \neq 0 \qquad (28, 29, 30, 31)$$

A set of bare conductive elements arbitrarily spaced can be specified as:

$$E_{Z,m}^{(\alpha)} = A_m^{(\alpha)} H_m^{(1)}(\lambda r_\alpha) + \qquad (32, 33)$$

$$\sum_{\beta=1}^{N} \sum_{n=-\infty}^{\infty} A_n^{(\beta)} (-1)^m e^{i(n-m)\theta_{\beta\alpha}} H_{n-m}^{(1)}(\lambda d_{\beta\alpha}) J_{-m}(\lambda r_\alpha)$$

$$H_{\theta,m}^{(\alpha)} = \left(\frac{-ik^2}{\mu\omega\lambda}\right) \left\{ A_m^{(\alpha)} \frac{\partial H_m^{(1)}(\lambda r_\alpha)}{\partial \lambda r_\alpha} + \right.$$

$$\left. \sum_{\beta=1}^{N} \sum_{n=-\infty}^{\infty} A_n^{(\beta)} (-1)^m e^{i(n-m)\theta_{\beta\alpha}} H_{n-m}^{(1)}(\lambda d_{\beta\alpha}) \frac{\partial J_{-m}(\lambda r_\alpha)}{\partial \lambda r_\alpha} \right\},$$

where $H_m^{(1)}$ is the first kind Hankel function at m order to satisfy proper behavior at infinity, $J_{-m}$ is the first kind Bessel function at m order, $\alpha$ is the considered conductive element and $\beta$ indicates surrounding conductive elements. Once $E_{Z,m}^{(\alpha)}$ and $H_{\theta,m}^{(\alpha)}$ are known for any $\alpha$ conductive element, the impedance matrix in Fourier domain $Z_D(k_3)$ can be simply calculated by the classical relation between magnetic and electric field provided by Equation (2). In order to find the impedance matrix $Z_T$ in space, a simple inverse Fourier transform can be used. The same approach can be used to construct the impedance matrix $Z_C$ associated with the material within the surface of the conductive element.

For these examples, the field can be finite at the center. Therefore, first kind Bessel functions can be used. Considering again a transverse magnetic formulation components of electric and magnetic field are:

$$E_Z^{\alpha_c} = \sum_{m=-\infty}^{\infty} J_m(\lambda_c r_\alpha) \qquad (34, 35)$$

$$H_\theta^{\alpha_c} = \frac{ik_c^2}{\mu_c \omega \lambda_c} \sum_{m=-\infty}^{\infty} \frac{\partial J_m(\lambda_c r_\alpha)}{\partial \lambda_c r_\alpha}$$

where $$k_c = \omega^2 \mu_c \left( \varepsilon_c + \frac{i\sigma_c}{\omega} \right). \qquad (36)$$

The impedance may then be calculated exactly, or alternatively, as for many conducting materials $\theta_c \Box \varepsilon_c \omega$ and an asymptotic expansion can be taken into account so:

$$Z_C(k_3) = \left(\frac{1-i}{2\pi r_\alpha}\right) \left(\frac{\omega \mu_c}{2\sigma_c}\right)^{\frac{1}{2}}. \qquad (37)$$

Using such a technique can provide several and decisive numerical advantages. For example, the expression of impedance matrix can be explicit in $k_3$ and the solution of the electromagnetic field can be analytical and valid for any desired distance between cables (increasing order of Hankel functions). Moreover, the transformation to physical space can be inexpensive if an inverse Fast Fourier Transform (FFT) is introduced.

In a practical example, the foregoing concepts can be applied to a five-wire cable ribbon in a reverberation chamber. The five wires are of equal radius, parallel to each other, and equally spaced in a single plane. This leads to a 5×5 impedance matrix $Z_D(k_3)$ relating the electric field on each wire to the surface magnetic fields. A grid of N evenly spaced points is then considered along each wire, and numerical Fourier transform techniques are employed to convert $Z_D(k_3)$ into a 5N×5N impedance matrix $Z_D$ that relates the surface magnetic and electric fields at each point. The same approach is also used to construct the impedance matrix $Z_C$.

Figure 4:
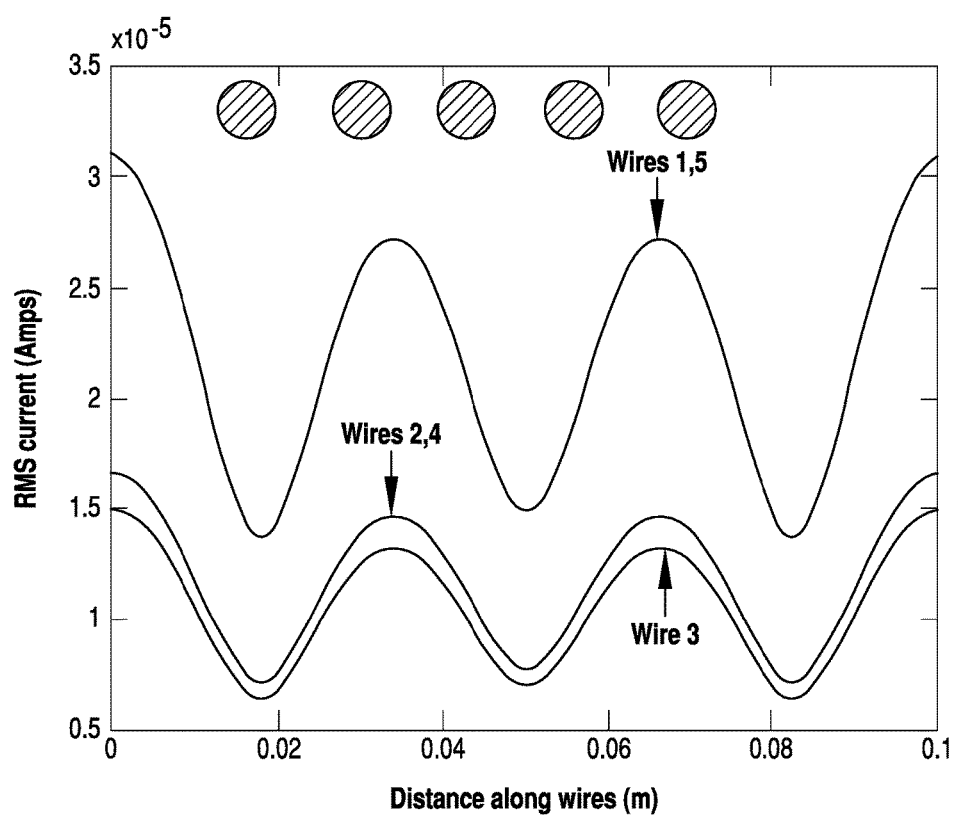
FIG. 4 illustrates a resulting root mean square current in each wire of five wires of an exemplary electrical system as a function of the distance along the wires in meters for a first spacing of the wires.
Figure 5:
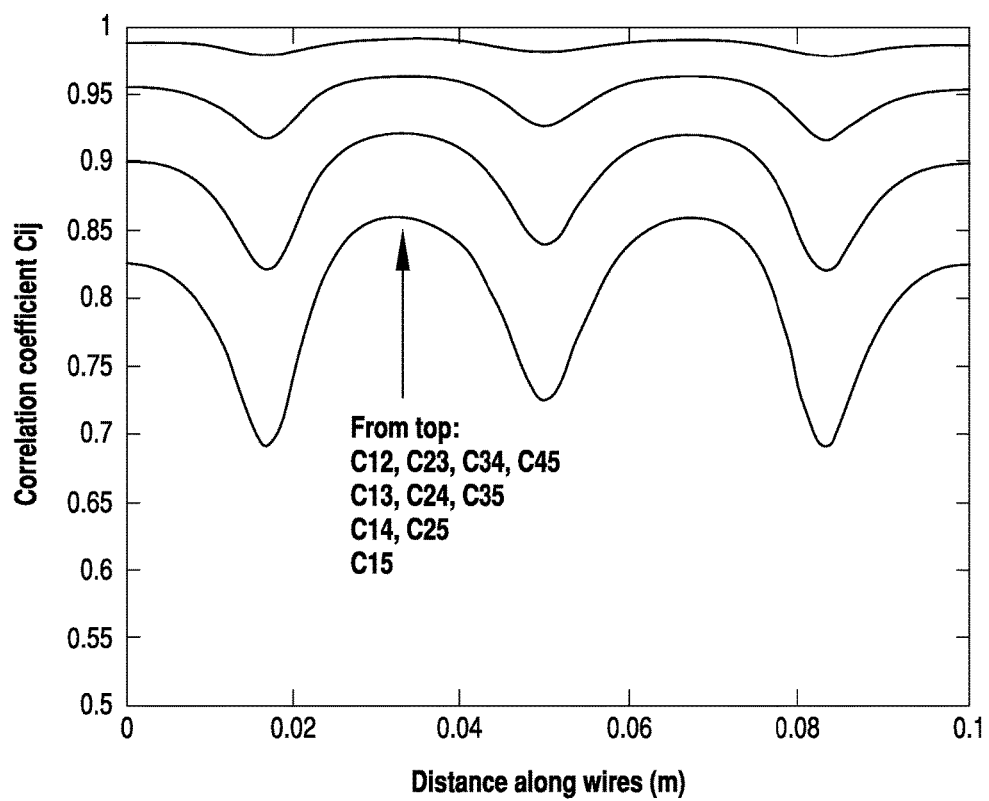
FIG. 5 illustrates current cross-correlation coefficients for the wires of FIG. 4 as a function of distance along the wires in meters.

Each end of each wire is earthed, and the wires are taken to have a radius of 0.19 millimeters and a length of 10 centimeters, and the spacing between the centers of any two neighboring wires is 1.27 millimeters. The power input to the reverberation room is supplied at $\omega=100$ c, corresponding to a frequency of 4.77 GigaHertz, and the power supplied is adjusted so that the reverberant field strength is $E[E.E]=1$ Volt$^2$/meter$^2$. No direct voltage is applied to the wires, meaning that $e_{app}=0$. The resulting root mean square current in each wire, as predicted by Equation (26), is shown at FIG. 4 as a function of the distance along the wires in meters. Meanwhile, the current cross-correlation coefficients (defined as $c_{ij}=E[h_i h_j]/E[h_i^2]^{1/2} E[h_j^2]^{1/2}$) are shown at FIG. 5 as a function of the distance along the wires in meters. It can be seen from FIG. 4 that the outer wires provide partial shielding of the inner wires, in that the root mean square current is least for the central wire (Wire 3). The results shown in FIG. 5 indicate that the correlation coefficients are all positive and reasonably large, which indicates that the loading excites predominantly in-phase (or antenna mode) currents in the wires.

Figure 6:
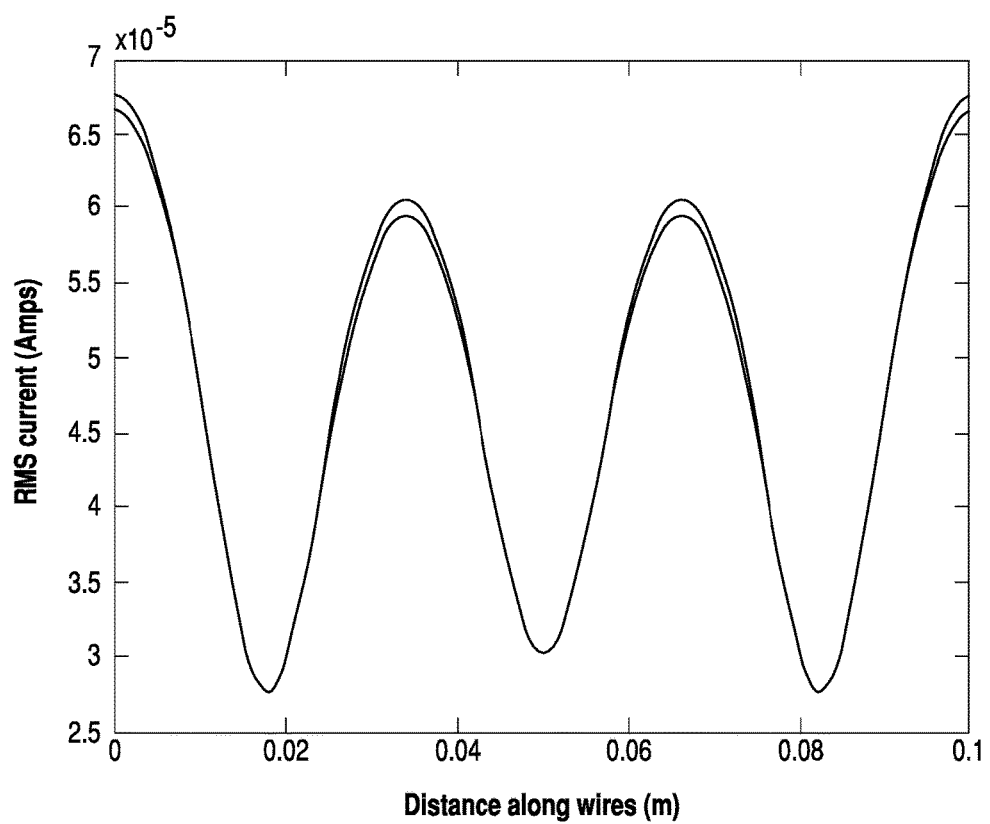
FIG. 6 illustrates a resulting root mean square current in each wire of five wires of the exemplary electrical system of FIGS. 4 & 5 as a function of the distance along the wires in meters for a second spacing of the wires.
Figure 7:
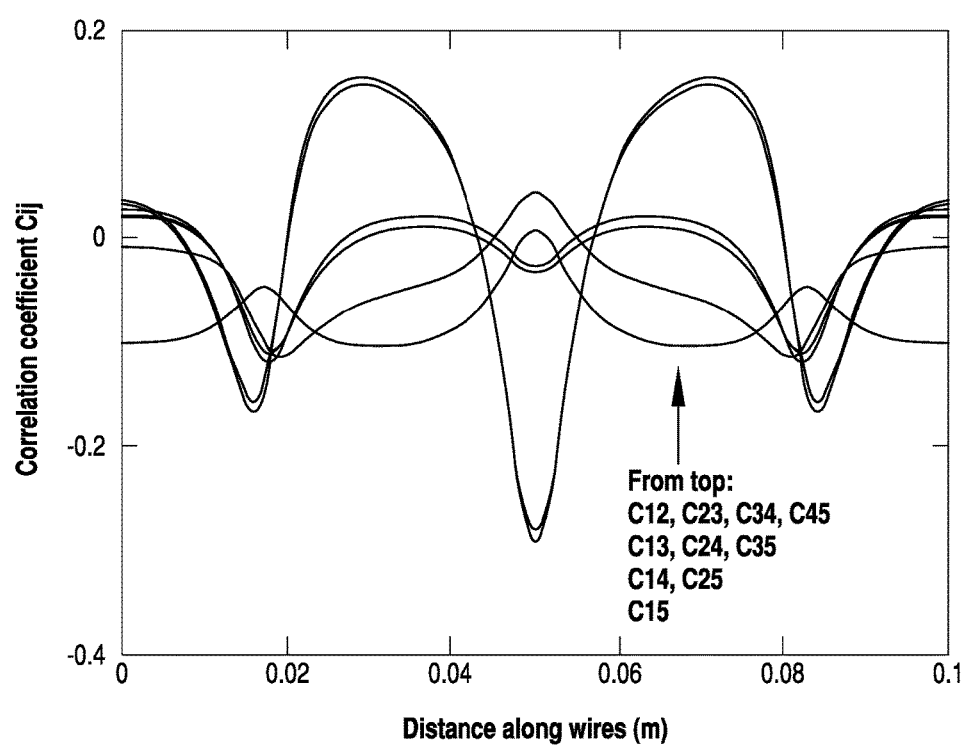
FIG. 7 illustrates current cross-correlation coefficients for the wires of FIG. 6 as a function of distance along the wires in meters.

The effect of increasing the gap between the wires to 6 centimeters is shown at FIGS. 6 and 7. The wavelength of the electromagnetic field in the cavity is 6.28 centimeters, and so the spacing is sufficiently great to eliminate significant shielding effects. For example, it can be seen from FIG. 6 that nearly identical root mean square currents are induced in each wire. In this case, the correlation between the currents in the various wires is relatively low, as can be seen at FIG. 7, with negative correlations appearing at some points along the wires. For example, Wire 1 and Wire 2 have a pronounced negative correlation at mid-span. The correlation between the currents in Wire 1 and Wire 5 never exceeds a magnitude of 0.1.

Finally, it can be noted the correlation matrix given by Equation (26) can be used to calculate the ensemble average of any quadratic function of the currents with the form $h^{*T}Ah$, including, for example, a mean square of a sum of the currents (in which case each entry of A is unity), and the mean squared value of the current in any particular transmission mode.

Next, the principles discussed above with respect to Equations (1)-(37) can be applied to electrical systems comprising conductive elements having one or more coatings (e.g., shielding and/or other dielectric coatings) using a transfer matrix that allows expressing a total external field as a function of layers generated fields. Once again, the conductive elements can be similar or identical to conductive element(s) 215.

For a conductive element having one or more coatings, the electromagnetic field (considering a transverse mode formulation) can be expressed for each j layer as:

$$E_{Z,m}^{(\alpha,j)} = A_m^{(\alpha,j)} H_m^{(1)}(\lambda_j r_{\alpha,j}) + C_m^{(\alpha,j)} H_m^{(2)}(\lambda_j r_{\alpha,j}) \quad (38, 39)$$

$$H_{\theta,m}^{(\alpha,j)} = \left(\frac{-ik^2}{\mu\omega\lambda}\right)\left\{A_m^{(\alpha,j)}\frac{\partial H_m^{(1)}(\lambda_j r_{\alpha,j})}{\partial \lambda r_{\alpha j}} + C_m^{(\alpha,j)}\frac{\partial H_m^{(2)}(\lambda_j r_{\alpha,j})}{\partial \lambda r_{\alpha j}}\right\}$$

where $H_m^{(2)}$ is the second kind Hankel function at m order. The presence of this additional term can take into account an inward propagating cylindrical wave. Due to continuity into the electromagnetic field, a chain of transfer matrix can be provided from previous equations. To clarify this concept, two generic adjacent layers j and j−1, due to field continuity, can be expressed as:

$$\begin{pmatrix} e_m^{(\alpha,j)} \\ h_m^{(\alpha,j)} \end{pmatrix} = G_m^{(\alpha,j)}(r_{\alpha j})\begin{pmatrix} A_m^{(\alpha,j)} \\ C_m^{(\alpha,j)} \end{pmatrix}\begin{pmatrix} e_m^{(\alpha,j-1)} \\ h_m^{(\alpha,j-1)} \end{pmatrix} = G_m^{(\alpha,j)}(r_{\alpha(j-1)})\begin{pmatrix} A_m^{(\alpha,j)} \\ C_m^{(\alpha,j)} \end{pmatrix}. \quad (40, 41)$$

Accordingly, the transfer matrix can be expressed as:

$$\begin{pmatrix} e_m^{(\alpha,j)} \\ h_m^{(\alpha,j)} \end{pmatrix} = T_m^{(\alpha,j)}\begin{pmatrix} e_m^{(\alpha,j)} \\ h_m^{(\alpha,j)} \end{pmatrix}, \quad (42)$$

where $$T_m^{(\alpha,j)} = G_m^{(\alpha,j)}(r_{\alpha j})[G_m^{(\alpha,j)}(r_{\alpha(j-1)})]^{-1} \quad (43)$$

When the transfer matrices are known, the impedance matrix $Z_C$ can be calculated as in previous sections.

Further, the principles discussed above with respect to Equations (1)-(43) can be applied to electrical systems comprising conductive elements in the vicinity of a wall or cavity surface. The wall and/or cavity surface can be similar or identical to wall(s) 212 (FIG. 2). Likewise, the conductive elements can be similar or identical to conductive element(s) 215. Further, the wall and/or cavity surface can be conductive or non-conductive. For example, if one or more conductive elements are in vicinity of a wall or cavity surface, the impedance matrices can be modified to account for a non-negligible wall effect.

When the wall or cavity surface is perfectly conductive, its effect can be accounted for by a mirror image technique. Namely, the wall effect can be accounted for by considering a mirror image of the concerned conductive element posed at an equal distance opposite the concerned conductive element respective to the wall or cavity surface. Then, the principles discussed above with respect to Equations (1)-(43) can be applied to define the relevant impedance matrices.

If the wall or cavity surface is not a perfect conductor, then the mirror image approach can be replaced with the use of a reflection coefficient. The reflection coefficient can have a modulus that is less than unity to allow for the fact that the wall or cavity surface does not provide perfect reflection of incident waves. As a result, the field associated with the mirror image of the conductive element is reduced.

Further still, the principles discussed above with respect to Equations (1)-(43) can be applied to electrical systems comprising conductive elements being bundled together and having two or more different coatings (e.g., e.g., shielding and/or other dielectric coatings). Specifically, by expressing the relevant equations of Equations (1)-(43) with m order Hankel expansions, as discussed above, any numbers of layers and any distances between conductive layers can be accommodated just by adding more terms to the expansion. Moreover, the mirror image techniques discussed above to account for a wall or cavity surface remain applicable to account for proximity to walls or cavity surfaces.

Even further still, the principles discussed above with respect to Equations (1)-(43) can be applied to electrical systems comprising any number of different electrical components coupled with conductive elements of the electrical systems. Once again, the conductive elements can be similar or identical to conductive element(s) 215. Further, each electrical component can be fully described by one or more multi-input/multi-output S-parameter models.

In general, imposing boundary conditions to an electrical system may not be a trivial task. If no consideration is made, a zero-current boundary condition can be imposed, which may not render accurate results. However, relaxing boundary conditions can solve this issue. A mirror image of a conductive element can be added at both ends of the conductive element, modifying the impendence matrices of the conductive element and imposing short-circuit conditions. Other boundary conditions can be considered by adding one or more additional matrices.

For example, an electric component can be considered as a boundary condition. That is, an additional electric field generated by current at the end of a conductive element can be represented. In this approach, a uniform surface electric field $e_{gen}(x)$ can be generated over a small region $-1 \leq x_3 \leq 1$. Uniform surface electric field $e_{gen}(x)$ can be proportional to the average current over this small region, so that:

$$e_{gen}(x_3) = \left(\frac{R}{l}\right)[He(x_3 + l) - He(x_3 - l)]\left\{\frac{1}{2l}\int_{-l}^{+l} h(x_3)\,dx_3\right\}, \quad (44)$$

where He is the heavy-side step function and R is an impedance (a real value of R would represent a resistance). The average current over the small region can be written in terms of the generalized current vector in the form $$\frac{1}{2l}\int_{-l}^{+l} h(x_3)\,dx_3 = c^T h. \quad (45)$$

Thus, to account for the effects of the electrical component, an impedance matrix $Z_R = Rcc^T$ can be added to impedance matrix $Z_D$ of the conductive element concerned.

Circling back now to measurement module 110 and electrical parameters module 111 in FIG. 1, given the foregoing context of the functionality of impedance matrix module 112, mean energy module 113, and energy variance module 114 as discussed above, measurement module 110 and electrical parameters module 111 can receive physical information about the electrical system from which impedance matrix module 112, mean energy module 113, and energy variance module 114 can perform the above described functionality. Notably, the functionality of impedance matrix module 112, mean energy module 113, and energy variance module 114 can be repeated for varying electrical parameter(s) of the electromagnetic wave creation element(s) of the electrical system provided by electrical parameters module 111 (i.e., multiple electric power levels, multiple electric frequencies, etc. of the electric waves emitted by the electromagnetic wave creation element(s)).

Meanwhile, modification module 115 can be operable to use the mean energy of the one or more electromagnetic fields in the conductive element(s) (e.g., as determined by mean energy module 113) and the energy variance of the one or more electromagnetic fields in the conductive element(s) (e.g., as determined by energy variance module 114) to determine one or more potential changes to at least one of (i) the one or more conductive elements, (ii) a region surrounding the one or more conductive elements, or (iii) the at least one electromagnetic wave creation element. These changes can be intended to mitigate or eliminate induced current in the electrical system to prevent damage to the electrical system and/or to prevent electrical interference with the electrical system. In other words, modification module 115 can be configured to indicate to a user of apparatus 100 how the electrical system could be reconfigured to prevent damage to the electrical system and/or to prevent electrical interference with the electrical system. Meanwhile, given these indications, the user can apply one or more of the potential changes, as desirable.

For example, exemplary changes can comprise adding one or more coatings (e.g., electromagnetic shield and/or other dielectric coatings) to the conductive element(s) and/or moving the conductive element(s) relative to the at least one electromagnetic wave creation element. Further exemplary changes can comprise moving the conductive element(s) relative to each other and/or if possible, moving one or more wall or cavity surfaces of the electrical system.

In many embodiments, in order to determine these changes, modification module 115 can be configured to model the electromagnetic field(s) in the conductive element(s) based upon the mean energy of the electromagnetic field(s) in the conductive element(s) and the energy variance of the electromagnetic field(s) in the conductive element(s). Meanwhile, after modeling the electromagnetic field(s), modification module 115 can determine confidence bands of a maximum energy of the electromagnetic fields in the one or more conductive elements. These confidence bands can be determined using Equations (26) and (27), or their relevant expanded and/or transformed variants, in the two parameter distribution mentioned above. Then, modification module 115 can determine a probability that the maximum energy of the electromagnetic field(s) in the conductive element(s) is equal to or greater than a predetermined energy level. When the probability that the maximum energy of the electromagnetic field(s) in the conductive element(s) is equal to or greater than the predetermined energy level is larger than a predetermine probability value, the modification module 115 can indicate changes to the electrical system that will lower the probability that the maximum energy of the electromagnetic field(s) in the conductive element(s) is equal to or greater than the predetermined energy level. In some embodiments, part of determining these changes can be implemented by simulating (e.g., iteratively) other configurations of the electrical system and comparing the configurations. In many embodiments, although the predetermined probability value can depend on the acceptable level of risk of damage and/or interference with the electrical system, in specific examples, the predetermined probability value can be approximately 1, 3, 5, 10, 20 or 50 percent.

Some embodiments also include a method of providing an apparatus. The apparatus can be similar or identical to apparatus 100 (FIG. 1). Accordingly, the method can comprise one or more activities of providing one or more modules of the apparatus, wherein the module(s) can be similar or identical to the module(s) of apparatus 100 (FIG. 1) as described above.

Figure 8:
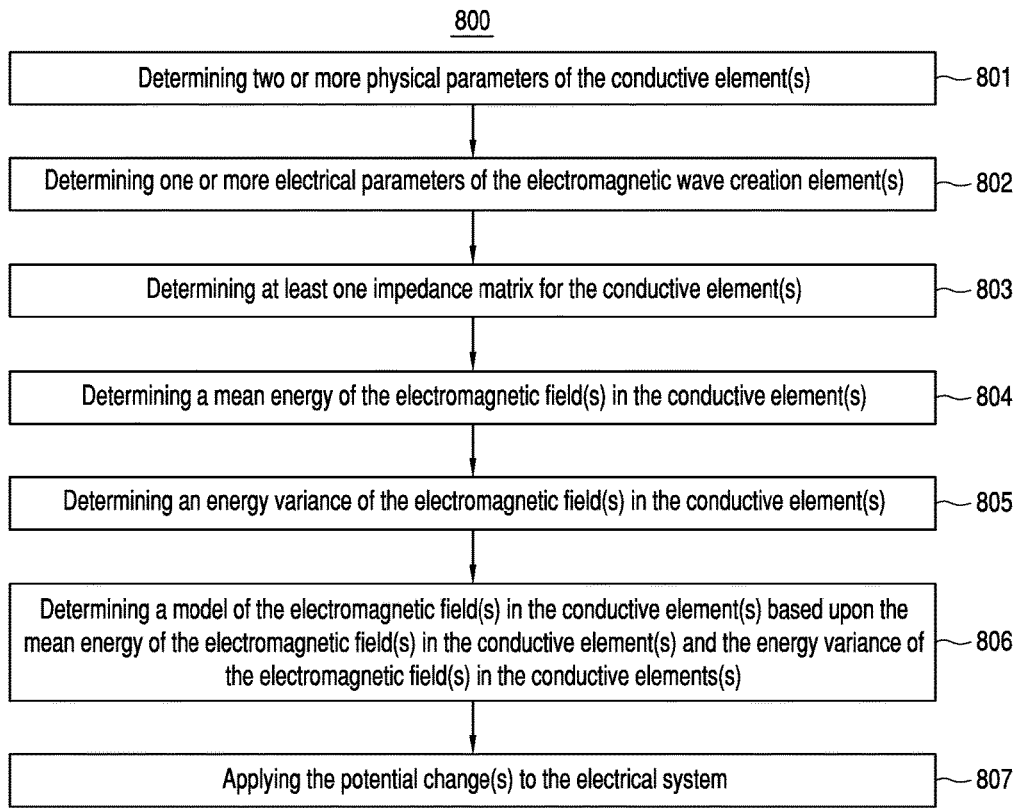
FIG. 8 illustrates a flow chart for an embodiment of a method of determining one or more electromagnetic fields in one or more conductive elements of an electrical system.

Turning ahead now in the drawings, FIG. 8 illustrates a flow chart for an embodiment of a method 800 of determining one or more electromagnetic fields in one or more conductive elements of an electrical system. The electromagnetic field(s) can be caused by one or more electrical waves emitted by at least one electromagnetic wave creation element of the electrical system. Method 800 is merely exemplary and is not limited to the embodiments presented herein. Method 800 can be employed in many different embodiments or examples not specifically depicted or described herein. In some embodiments, the activities, the procedures, and/or the processes of method 800 can be performed in the order presented. In other embodiments, the activities, the procedures, and/or the processes of method 800 can be performed in any other suitable order. In still other embodiments, one or more of the activities, the procedures, and/or the processes in method 800 can be combined or skipped.

In some embodiments, the conductive element(s) can be similar or identical to the conductive element(s) described above with respect to apparatus 100 (FIG. 1) and/or similar or identical to conductive element(s) 215 (e.g., conductive element 210 and/or conductive element 211). In these or other embodiments, the electrical system can be similar or identical to the electrical system described above with respect to apparatus 100 (FIG. 1) and/or similar or identical to electrical system 200 (FIG. 2). Further in these or in other embodiments, the electromagnetic wave creation element(s) can be similar or identical to the electromagnetic wave creation element(s) described above with respect to apparatus 100 (FIG. 1) and/or similar or identical to electromagnetic wave creation element(s) 203 (FIG. 2).

Figure 9:
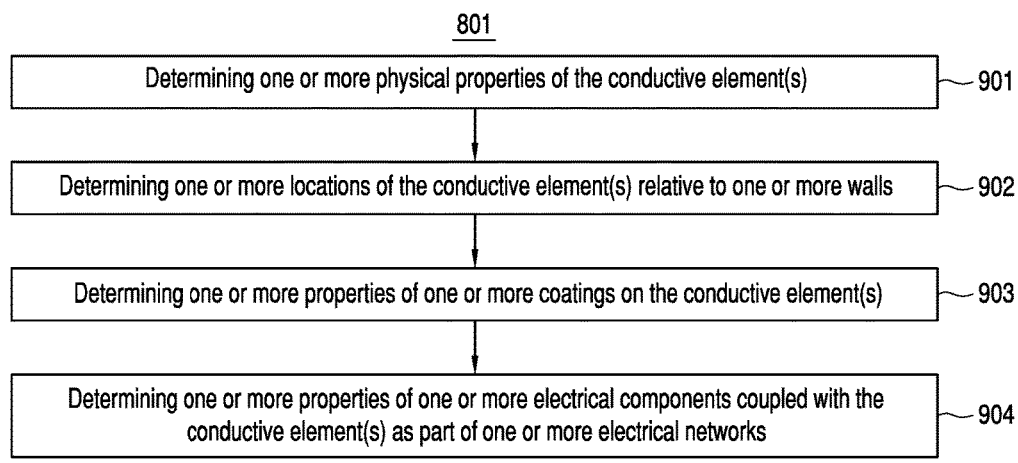
FIG. 9 illustrates an exemplary activity of determining two or more physical parameters of the conductive element(s), according to the embodiment of FIG. 8.

In many embodiments, method 800 can comprise activity 801 of determining two or more physical parameters of the conductive element(s). In many embodiments, the physical parameter(s) of the conductive element(s) can be similar or identical to the physical parameter(s) of the conductive element(s) described above with respect to apparatus 100 (FIG. 1). FIG. 9 illustrates an exemplary activity 801, according to the embodiment of FIG. 8.

For example, activity 801 can comprise activity 901 of determining one or more physical properties of the conductive element(s). In many embodiments, the physical properties of the conductive element(s) can be similar or identical to the physical properties of the conductive element(s) described above with respect to apparatus 100 (FIG. 1).

Further, activity 801 can comprise activity 902 of determining one or more locations of the conductive element(s) relative to one or more walls. In some embodiments, the wall(s) can be similar or identical to the wall(s) and/or cavity surface(s) described above with respect to apparatus 100 (FIG. 1) and/or similar or identical to wall(s) 212 (FIG. 2).

Further still, activity 801 can comprise activity 903 of determining one or more properties of one or more coatings on the conductive element(s). In some embodiments, the one or more properties of one or more coating(s) on the conductive element(s) can be similar or identical to the one or more properties of one or more coating(s) on the conductive element(s) described above with respect to apparatus 100 (FIG. 1).

Even further still, activity 801 can comprise activity 904 of determining one or more properties of one or more electrical components coupled with the conductive element(s) as part of one or more electrical networks. In some embodiments, the electrical component(s) can be similar or identical to the electrical component(s) described above with respect to apparatus 100 (FIG. 1) and/or electrical system 200 (FIG. 2).

Turning now back to FIG. 8, method 800 can comprise activity 802 of determining one or more electrical parameters of the electromagnetic wave creation element(s). In some embodiments, performing activity 802 can comprise (i) determining an electric power of one or more frequencies of the electromagnetic wave(s) emitted by the electromagnetic wave creation element(s) and/or (ii) determining at least one frequency of interest from the one or more frequencies of the electromagnetic wave(s) emitted by the electromagnetic wave creation element(s).

Figure 10:
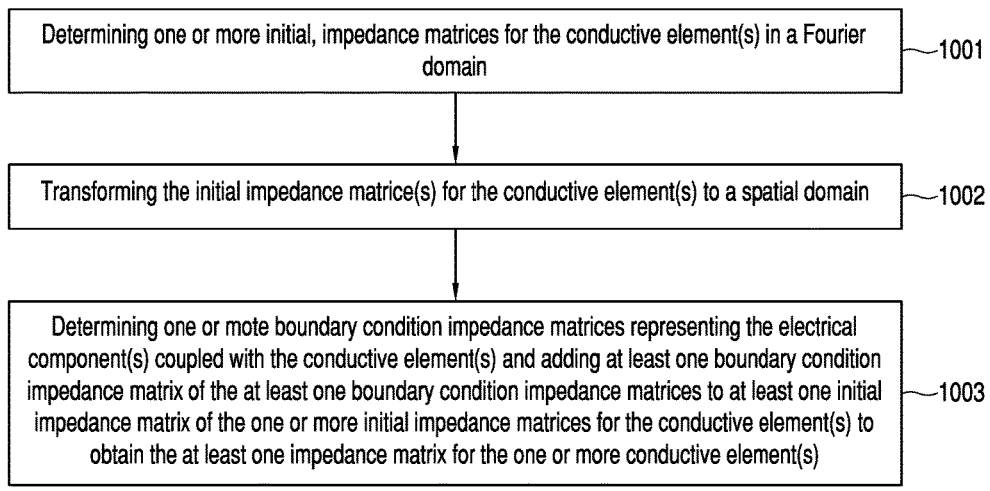
FIG. 10 illustrates an exemplary activity of determining at least one impedance matrix for the conductive element(s), according to the embodiment of FIG. 8.

Further, method 800 can comprise activity 803 of determining at least one impedance matrix for the conductive element(s). In some embodiments, performing activity 803 can be similar or identical to determining at least one impedance matrix for the conductive element(s) as described above with respect to apparatus 100 (FIG. 1). FIG. 10 illustrates an exemplary activity 803, according to the embodiment of FIG. 8.

For example, activity 803 can comprise activity 1001 of determining one or more initial impedance matrices for the conductive element(s) in a Fourier domain; activity 1002 of transforming the one or more initial impedance matrices for the conductive element(s) to a spatial domain; and/or activity 1003 of determining one or more boundary condition impedance matrices representing the electrical component(s) coupled with the conductive element(s) and adding at least one boundary condition impedance matrix of the at least one boundary condition impedance matrices to at least one initial impedance matrix of the one or more initial impedance matrices for the conductive element(s) to obtain the at least one impedance matrix for the one or more conductive element(s). In some embodiments, activity 803 can be omitted.

Turning again to FIG. 8, method 800 can comprise activity 804 of determining a mean energy of the electromagnetic field(s) in the conductive element(s). In some embodiments, performing activity 804 can comprise determining a mean value of a cross-spectrum of one or more electric currents in the conductive element(s). In some embodiments, activity 804 can be omitted.

Further, method 800 can comprise activity 805 of determining an energy variance of the electromagnetic field(s) in the conductive element(s). In some embodiments, performing activity 805 can comprise determining an energy variance of a cross-spectrum of one or more electric currents in the conductive element(s). In some embodiments, activity 805 can be omitted.

Meanwhile, method 800 can comprise activity 806 of using the mean energy of the electromagnetic field(s) in the conductive element(s) and the energy variance of the electromagnetic field(s) in the conductive element(s) to determine one or more potential changes to (i) the conductive element(s), (ii) a region surrounding the conductive element(s), and/or (iii) the electromagnetic wave creation element(s). Notably, in many embodiments, activity 806 can be performed after one or more of activities 801-805. Further, the potential change(s) can be similar or identical to the potential change(s) discussed above with respect to apparatus 100 (FIG. 1).

Figure 11:
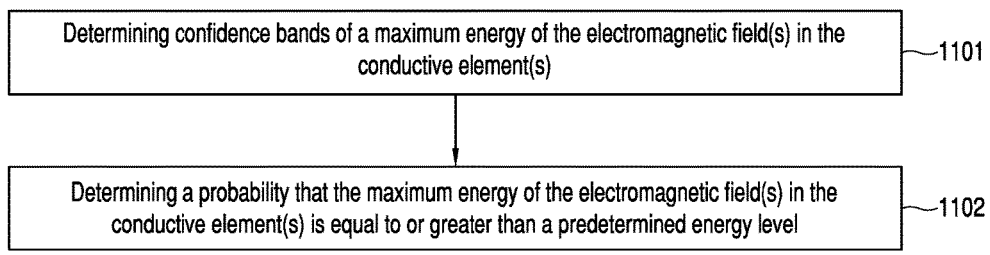
FIG. 11 illustrates an exemplary activity of determining a model of the electromagnetic field(s) in the conductive element(s) based upon a mean energy of the electromagnetic field(s) in the conductive element(s) and an energy variance of the electromagnetic field(s) in the conductive element(s), according to a embodiment.

In some embodiments, performing activity 806 can comprise determining a model of the electromagnetic field(s) in the conductive element(s) based upon the mean energy of the electromagnetic field(s) in the conductive element(s) and the energy variance of the electromagnetic field(s) in the conductive element(s). FIG. 11 illustrates an exemplary activity 1100 of determining a model of the electromagnetic field(s) in the conductive element(s) based upon the mean energy of the electromagnetic field(s) in the conductive element(s) and the energy variance of the electromagnetic field(s) in the conductive element(s), according to the embodiment of FIG. 8.

For example, activity 1100 can comprise activity 1101 of determining confidence bands of a maximum energy of the electromagnetic field(s) in the conductive element(s). Further, activity 1100 can comprise activity 1102 of determining a probability that the maximum energy of the electromagnetic field(s) in the conductive element(s) is equal to or greater than a predetermined energy level. When the probability that the maximum energy of the one or more electromagnetic fields in the one or more conductive elements is equal to or greater than the predetermined energy level is larger than a predetermine value, activity 807 (FIG. 8) can be performed.

Turning back to FIG. 8, method 800 can comprise activity 807 of applying the potential change(s) to the electrical system. In many embodiments, activity 807 can be performed after activity 806.

In many embodiments, at least part of activity 801, activity 802, activity 803, activity 804, activity 805, activity 806, activity 901, activity 902, activity 903, activity 904, activity 1001, activity 1002, activity 1003, activity 1101, and/or activity 1102 can be performed using a processing module. The processing module can be similar or identical to processing module 190 (FIG. 1). In some embodiments, activity 803, activity 804, and activity 805 can be performed multiple times for multiple electromagnetic frequencies of the electromagnetic waves.

Figure 12:
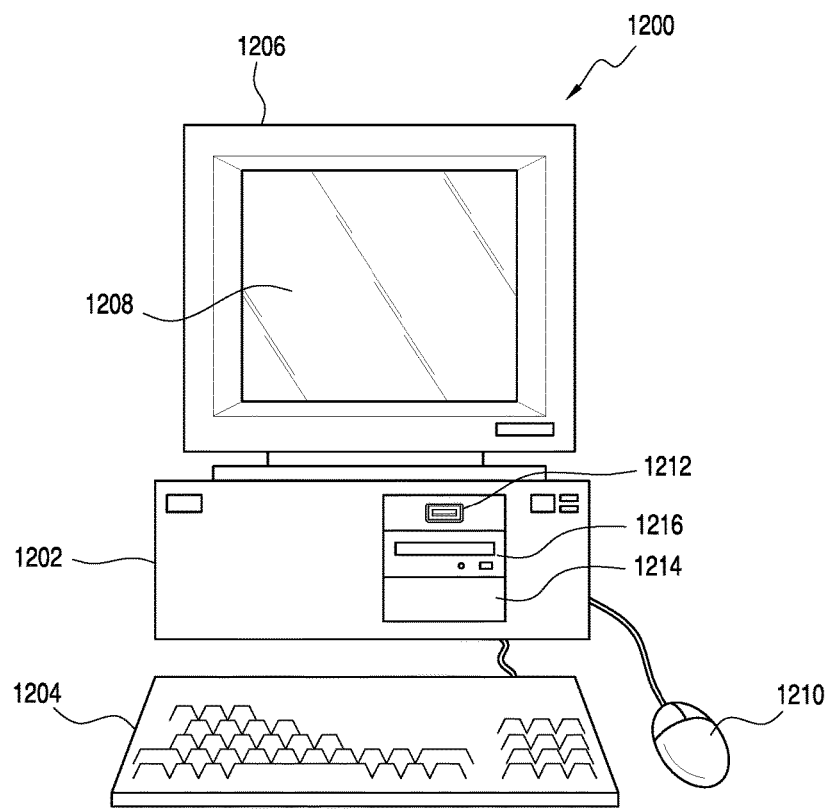
FIG. 12 illustrates an exemplary computer system that is suitable for implementing an embodiment of a computer system of the apparatus of FIG. 1, the method of FIG. 8, and/or the activity of FIG. 11.
Figure 13:
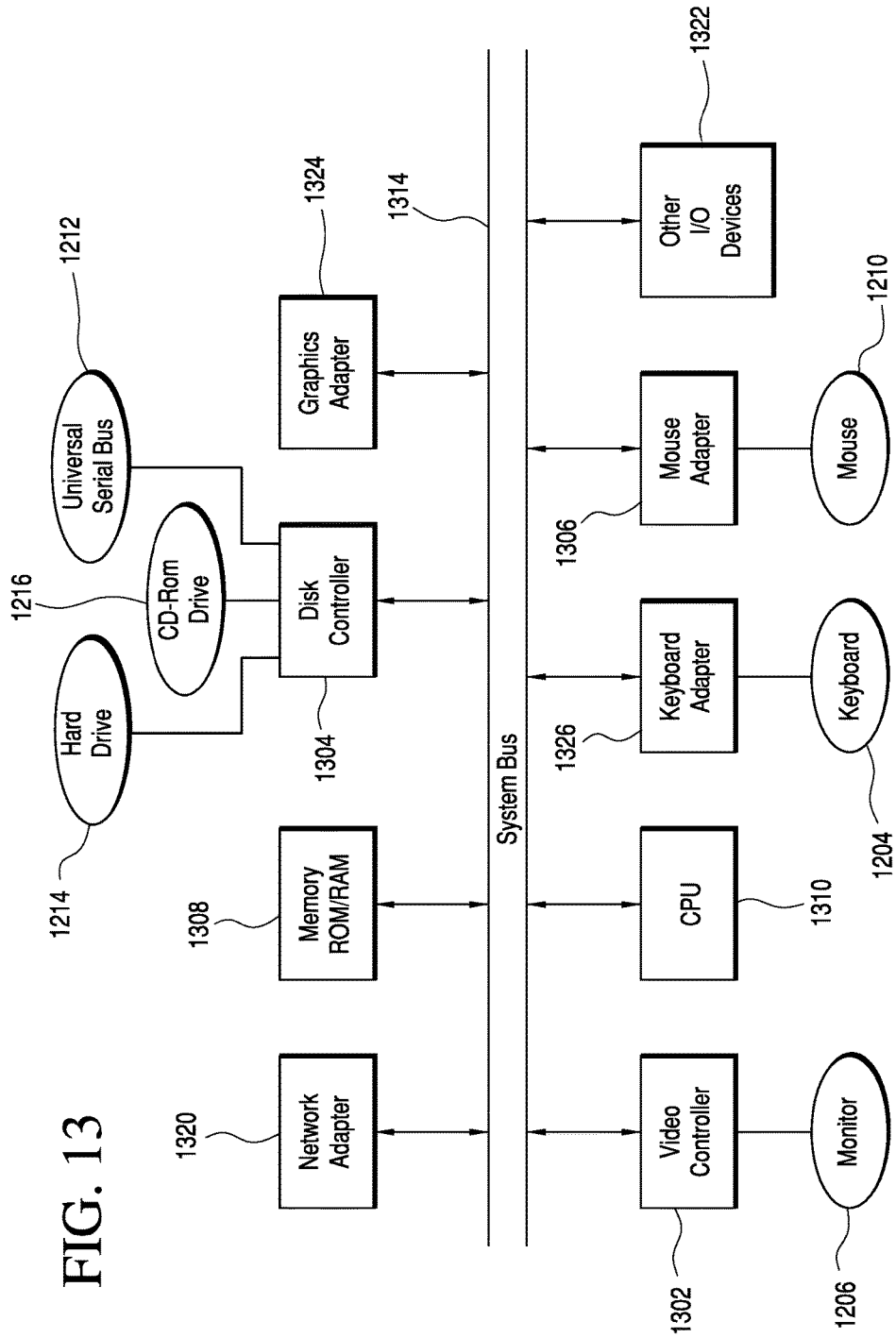
FIG. 13 illustrates a representative block diagram of an example of the elements included in the circuit boards inside a chassis of the computer system of FIG. 12.

Turning ahead now in the drawings, FIG. 12 illustrates a computer system 1200 that is suitable for implementing an embodiment of at least a portion of the computer system of apparatus 100 (FIG. 1) and/or for performing at least part of method 800 (FIG. 8). Computer 1200 includes a chassis 1202 containing one or more circuit boards (not shown), a USB (universal serial bus) port 1212, a Compact Disc Read-Only Memory (CD-ROM) and/or Digital Video Disc (DVD) drive 1216, and a hard drive 1214. A representative block diagram of the elements included on the circuit boards inside chassis 1202 is shown in FIG. 13. A central processing unit (CPU) 1310 in FIG. 13 is coupled to a system bus 1314 in FIG. 13. In various embodiments, the architecture of CPU 1310 can be compliant with any of a variety of commercially distributed architecture families.

System bus 1314 also is coupled to memory 1308 that includes both read only memory (ROM) and random access memory (RAM). Non-volatile portions of memory 1308 or the ROM can be encoded with a boot code sequence suitable for restoring computer system 1200 (FIG. 12) to a functional state after a system reset. In addition, memory 1308 can include microcode such as a Basic Input-Output System (BIOS). In some examples, memory 1108, USB in USB port 1112, hard drive 1114, and/or CD-ROM or DVD drive 1116 can be part of a storage module of computer system 1200. Storage module 191 (FIG. 1) can be similar or identical to the storage module of computer system 1200 (FIG. 12).

In the depicted embodiment of FIG. 13, various I/O devices such as a disk controller 1304, a graphics adapter 1324, a video controller 1302, a keyboard adapter 1326, a mouse adapter 1306, a network adapter 1320, and other I/O devices 1322 can be coupled to system bus 1314. Keyboard adapter 1326 and mouse adapter 1306 are coupled to a keyboard 1204 (FIGS. 12 and 13) and a mouse 1210 (FIGS. 12 and 13), respectively, of computer system 1200 (FIG. 12). While graphics adapter 1324 and video controller 1302 are indicated as distinct units in FIG. 13, video controller 1302 can be integrated into graphics adapter 1324, or vice versa in other embodiments. Video controller 1302 is suitable for refreshing a monitor 1206 (FIGS. 12 and 13) to display images on a monitor 1206 (FIG. 12) of computer system 1200 (FIG. 12). Disk controller 1304 can control hard drive 1214 (FIGS. 12 and 13), USB port 1212 (FIGS. 12 and 13), and CD-ROM or DVD drive 1216 (FIGS. 12 and 13). In other embodiments, distinct units can be used to control each of these devices separately.

Although many other components of computer system 1200 (FIG. 12) are not shown, such components and their interconnection are well known to those of ordinary skill in the art. Accordingly, further details concerning the construction and composition of computer system 1200 and the circuit boards inside chassis 1202 (FIG. 12) need not be discussed herein.

When computer system 1200 in FIG. 12 is running, program instructions stored on stored on a USB drive in USB port 1212, on a CD-ROM or DVD in CD-ROM and/or DVD drive 1216, on hard drive 1214, or in memory 1308 (FIG. 13) are executed by CPU 1310 (FIG. 13). A portion of the program instructions, stored on these devices, can be suitable for carrying out at least part of method 800 (FIG. 8).

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that any of the activities of method 800 (FIG. 8) and/or of activity 1000 (FIG. 10) may be comprised of many different activities and be performed by many different modules, and in many different orders, that any element of FIGS. 1-13 may be modified, and that the foregoing discussion of certain of these embodiments does not necessarily represent a complete description of all possible embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. An apparatus configured to determine one or more electromagnetic fields in one or more conductive elements of an electrical system, the one or more electromagnetic fields being caused by one or more electrical waves emitted by at least one electromagnetic wave creation element of the electrical system, the apparatus comprising:
   one or more physical parameter sensors configured to measure physical parameters of the one or more conductive elements of the electrical system;
   one or more electrical parameter sensors configured to measure electrical parameters of the at least one electromagnetic wave creation element of the electrical system;
   a processing module; and
   a non-transitory memory storage module storing computer instructions configured to run on the processing module, the processing module being configured to:
      receive from the one or more physical parameter sensors two or more physical parameters of the one or more conductive elements;
      receive from the one or more electrical parameter sensors one or more electrical parameters of the at least one electromagnetic wave creation element;
      determine and store in memory at least one impedance matrix for the one or more conductive elements based on the two or more physical parameters and the one or more electrical parameters of the one or more conductive elements, the at least one impedance matrix representing electrical properties of the one or more conductive elements;
      determine and store in memory a mean energy of the one or more electromagnetic fields in the one or more conductive elements based on the at least one impedance matrix for the one or more conductive elements; and
      determine and store in memory an energy variance of the one or more electromagnetic fields in the one or more conductive elements based on the at least one impedance matrix for the one or more conductive elements;
      determine, based on the mean energy and the energy variance of the one or more electromagnetic fields in the one or more conductive elements, one or more changes to at least one of (i) the one or more conductive elements, (ii) a region surrounding the one or more conductive elements, and (iii) the at least one electromagnetic wave creation element
      determine a model of the one or more changes to the at least one of (i) the one or more conductive elements, (ii) a region surrounding the one or more conductive elements, and (iii) the at least one electromagnetic wave creation element.

2. The apparatus of claim 1 further comprising:
   a display device coupled to the processing module;
   wherein:
      the acts further comprise displaying the model at the display device.

3. The apparatus of claim 1 wherein at least one of:
   the one or more conductive elements are located in one of:
      a vehicle comprising one of an automobile, an aircraft, or a ship; or
      an immobile structure; or
      the at least one electromagnetic wave creation element comprises at least one of a mobile communications device, an electromagnetic pulse weapon, or lightning.

4. The apparatus of claim 1 wherein:
each conductive element of the one or more conductive elements comprises an electrically conductive core and at least one coating.

5. The apparatus of claim 1 wherein:
the electrical system further comprises one or more conducting walls; and
the one or more conductive elements are in proximity to the one or more conducting walls.

6. The apparatus of claim 1 wherein:
the one or more conductive elements are bundled together in a bundle; and
each conductive element of the one or more conductive elements comprises one or more shielding layers.

7. The apparatus of claim 1 wherein:
the electrical system further comprises one or more electrical components; and
at least one of the one or more conductive elements is coupled with the one or more electrical components.

8. A method of determining one or more electromagnetic fields in one or more conductive elements of an electrical system, the one or more electromagnetic fields being caused by one or more electrical waves emitted by at least one electromagnetic wave creation element of the electrical system, the method comprising:
determining, using one or more physical parameter sensors, two or more physical parameters of the one or more conductive elements;
determining, using one or more electrical parameter sensors, one or more electrical parameters of the at least one electromagnetic wave creation element;
executing one or more first computer instructions configured to determine and store in memory at least one impedance matrix for the one or more conductive elements based on the two or more physical parameters and the one or more electrical parameters of the one or more conductive elements, the at least one impedance matrix representing electrical properties of the one or more conductive elements;
executing one or more second computer instructions configured to determine and store in memory a mean energy of the one or more electromagnetic fields in the one or more conductive elements based on the at least one impedance matrix for the one or more conductive elements;
executing one or more third computer instructions configured to determine and store in memory an energy variance of the one or more electromagnetic fields in the one or more conductive elements based on the at least one impedance matrix for the one or more conductive elements; and
executing one or more fourth computer instructions configured to use the mean energy and the energy variance of the one or more electromagnetic fields in the one or more conductive elements to determine one or more potential changes to at least one of (i) the one or more conductive elements and (ii) a region surrounding the one or more conductive elements;
wherein:
the one or more first computer instructions, the one or more second computer instructions, the one or more third computer instructions, and the one or more fourth computer instructions are configured to run at a processing module and configured to be stored at a non-transitory memory storage module, and the processing module is configured to perform the acts of the one or more first computer instructions, the one or more second computer instructions, the one or more third computer instructions, and the one or more fourth computer instructions; and
determining the one or more potential changes includes (i) modeling respective electromagnetic fields in the one or more conductive elements based on the mean energy of the one or more electromagnetic fields in the one or more conductive elements and the energy variance of the one or more electromagnetic fields in the one or more conductive elements, (ii) determining confidence bands of a maximum energy of the respective electromagnetic fields of the one or more conductive elements, and (iii) determining a probability that the maximum energy is equal to or greater than a predetermined energy level.

9. The method of claim 8 wherein:
the one or more potential changes comprise at least one of:
adding electromagnetic shielding to the one or more conductive elements; or
moving the one or more conductive elements relative to the at least one electromagnetic wave creation element.

10. The method of claim 8 further comprising:
applying the one or more potential changes to the electrical system.

11. The method of claim 8 wherein:
executing the one or more first computer instructions, executing the one or more second computer instructions, and executing the one or more third computer instructions are performed for two or more electromagnetic frequencies.

12. The method of claim 8 further comprising:
executing one or more fourth computer instructions configured to determine a model of the one or more electromagnetic fields in the one or more conductive elements based upon (i) the mean energy of the one or more electromagnetic fields in the one or more conductive elements and (ii) the energy variance of the one or more electromagnetic fields in the one or more conductive elements.

13. The method of claim 12 wherein:
executing the one or more fourth computer instructions comprises:
executing one or more fifth computer instructions configured to determine confidence bands of a maximum energy of the one or more electromagnetic fields in the one or more conductive elements; and
executing one or more sixth computer instructions configured to determine a probability that the maximum energy of the one or more electromagnetic fields in the one or more conductive elements is equal to or greater than a predetermined energy level.

14. The method of claim 13 further comprising:
when the probability that the maximum energy of the one or more electromagnetic fields in the one or more conductive elements is equal to or greater than the predetermined energy level is larger than a predetermined value, applying one or more potential changes to at least one of (i) the one or more conductive elements, and (ii) a region surrounding the one or more conductive elements.

15. The method of claim 8 wherein:
determining the two or more physical parameters of the one or more conductive elements comprises determining at least one of:

one or more physical properties of the one or more conductive elements;

one or more locations of the one or more conductive elements relative to one or more walls;

one or more properties of one or more coatings on the one or more conductive elements; or one or more properties of one or more electrical components coupled with the one or more conductive elements as part of one or more electrical networks.

16. The method of claim 15 wherein:

the one or more physical properties of the one or more conductive elements comprises at least one of:

one or more diameters of the one or more conductive elements;

one or more lengths of the one or more conductive elements; or one or more material properties of the one or more conductive elements.

17. The method of claim 8 wherein:

executing the one or more first computer instructions comprises:

executing one or more fourth computer instructions configured to determine one or more initial impedance matrices for the one or more conductive elements in a Fourier domain;

executing one or more fifth computer instructions configured to transform the one or more initial impedance matrices for the one or more conductive elements to a spatial domain; and executing one or more sixth computer instructions configured to determine one or more boundary condition impedance matrices representing one or more electrical components coupled with the one or more conductive elements and adding at least one boundary condition impedance matrix of the one or more boundary condition impedance matrices to at least one initial impedance matrix of the one or more initial impedance matrices for the one or more conductive elements to obtain the at least one impedance matrix for the one or more conductive elements.

18. The method of claim 8 wherein:

determining the one or more electrical parameters of the at least one electromagnetic wave creation element comprises at least one of:

determining an electric power of one or more frequencies of the one or more electromagnetic waves emitted by the at least one electromagnetic wave creation element; or determining at least one frequency of interest from the one or more frequencies of the one or more electromagnetic waves emitted by the electromagnetic wave creation element.

19. The method of claim 8 wherein:

executing the one or more second computer instructions comprises:

executing one or more fourth computer instructions determining a mean value of a cross-spectrum of one or more electric currents in the one or more conductive elements.

20. The method of claim 8 wherein:

executing the one or more third computer instructions comprises:

executing one or more fourth computer instructions configured to determine an energy variance of a cross-spectrum of one or more electric currents in the one or more conductive elements.

21. A method of determining one or more electromagnetic fields in one or more wires of an electrical system, the one or more electromagnetic fields being caused by one or more electrical waves emitted by at least one electromagnetic wave creation element of the electrical system, the method comprising:

executing one or more first computer instructions configured to identify, using one or more physical parameter sensors, two or more physical parameters of the one or more wires;

executing one or more second computer instructions configured to identify, using one or more electrical parameter sensors, one or more electrical parameters of the at least one electromagnetic wave creation element;

executing one or more third computer instructions configured to determine and store in memory at least one impedance matrix for the one or more conductive elements based on the two or more physical parameters and the one or more electrical parameters of the one or more conductive elements, the at least one impedance matrix representing electrical properties of the one or more conductive elements;

executing one or more fourth computer instructions configured to determine and store in memory a mean energy of the one or more electromagnetic fields in the one or more wires based on the at least one impedance matrix for the one or more conductive elements;

executing one or more fifth computer instructions configured to use the mean energy of the one or more electromagnetic fields in the one or more wires to determine one or more potential changes to at least one of (i) the one or more wires, (ii) a region surrounding the one or more wires, or (iii) the at least one electromagnetic wave creation element; and executing one or more sixth computer instructions configured to model the one or more potential changes;

wherein:

the one or more first computer instructions, the one or more second computer instructions, the one or more third computer instructions, the one or more fourth computer instructions, the one or more fifth computer instructions, and the one or more sixth computer instructions are configured to run at a processing module and configured to be stored at a non-transitory memory storage module, and the processing module is configured to perform the acts of the one or more first computer instructions, the one or more second computer instructions, the one or more third computer instructions, the one or more fourth computer instructions, the one or more fifth computer instructions, and the one or more sixth computer instructions; and modeling the one or more potential changes includes (i) modeling respective electromagnetic fields in the one or more conductive elements based on the mean energy of the one or more electromagnetic fields in the one or more conductive elements (ii) determining confidence bands of a maximum energy of the respective electromagnetic fields of the one or more conductive elements, and (iii) determining a probability that the maximum energy is equal to or greater than a predetermined energy level.

* * * * *